(12) United States Patent
Falb et al.

(10) Patent No.: US 11,964,116 B2
(45) Date of Patent: *Apr. 23, 2024

(54) GUIDE CATHETER CONTROL FLEXIBLE TRACK

(71) Applicant: Corindus, Inc., Waltham, MA (US)

(72) Inventors: Peter Falb, Hingham, MA (US); Adam Young, Dedham, MA (US); Kevin Bagley, Dedham, MA (US); Erin-Anne Lemieux, Mont Vernon, NH (US); Christopher Labak, Brookline, NH (US); Steven J. Blacker, Framingham, MA (US); Michael Atlas, Arlington, MA (US)

(73) Assignee: Corindus, Inc., Newton, MA (US)

( * ) Notice: Subject to any disclaimer, the term of this patent is extended or adjusted under 35 U.S.C. 154(b) by 216 days.

This patent is subject to a terminal disclaimer.

(21) Appl. No.: 17/301,855

(22) Filed: Apr. 16, 2021

(65) Prior Publication Data

US 2021/0228841 A1    Jul. 29, 2021

Related U.S. Application Data

(63) Continuation of application No. 15/913,136, filed on Mar. 6, 2018, now Pat. No. 11,007,348, which is a
(Continued)

(51) Int. Cl.
*A61M 25/02* (2006.01)
*A61B 17/00* (2006.01)
(Continued)

(52) U.S. Cl.
CPC ............. *A61M 25/02* (2013.01); *A61B 34/25* (2016.02); *A61B 34/30* (2016.02);
(Continued)

(58) Field of Classification Search
CPC ............. A61M 25/02; A61M 25/09041; A61M 39/06; A61M 25/0113; A61M 2210/125;
(Continued)

(56) References Cited

U.S. PATENT DOCUMENTS 4,593,967 A   6/1986 Haugen
4,988,356 A   1/1991 Crittenden et al.
(Continued)

FOREIGN PATENT DOCUMENTS

CN   1822876      8/2006
JP   S63229066    9/1988
(Continued)

OTHER PUBLICATIONS

International Search Report and Written Opinion for PCT/US2014/060664; dated Jan. 26, 2015; 7 pages.
(Continued)

*Primary Examiner* — Lauren P Farrar

(57) ABSTRACT

A system for controlling a hemostasis valve includes a hemostasis valve having a body portion having a proximal end, a distal end and a lumen extending between the proximal end and the distal end. The hemostasis value further includes at least one valve positioned in the proximal end of the body portion and an engagement member operatively coupled to the at least one valve. The system further includes a first drive member coupled to the engagement member and a controller coupled to the first drive member. The controller is configured to control the first drive member to impart movement to the engagement member to open and close the at least one valve.

19 Claims, 19 Drawing Sheets

Related U.S. Application Data continuation of application No. 15/029,115, filed on Apr. 13, 2016, now Pat. No. 10,549,071, application No. 17/301,855 is a continuation of application No. 15/029,115, filed as application No. PCT/US2014/060664 on Oct. 15, 2014, now Pat. No. 10,549,071.

(60) Provisional application No. 61/952,872, filed on Mar. 14, 2014, provisional application No. 61/891,389, filed on Oct. 15, 2013.

(51) Int. Cl.
*A61B 34/00* (2016.01)
*A61B 34/30* (2016.01)
*A61M 25/01* (2006.01)
*A61M 25/09* (2006.01)
*A61M 39/06* (2006.01)

(52) U.S. Cl.
CPC .. *A61M 25/0113* (2013.01); *A61M 25/09041* (2013.01); *A61M 39/06* (2013.01); *A61B 2017/00738* (2013.01); *A61B 2034/301* (2016.02); *A61M 2210/125* (2013.01)

(58) Field of Classification Search
CPC .... A61M 39/0606; A61B 34/25; A61B 34/30; A61B 2017/00738; A61B 2034/301; A61B 2017/00477
See application file for complete search history.

(56) References Cited

U.S. PATENT DOCUMENTS

| | | | |
|---|---|---|---|
| 5,167,636 A * | 12/1992 | Clement | A61M 39/0613 604/167.03 |
| 5,338,314 A | 8/1994 | Ryan | |
| 5,352,215 A | 10/1994 | Thome et al. | |
| 5,427,107 A | 6/1995 | Milo et al. | |
| 5,897,533 A * | 4/1999 | Glickman | A61M 39/0613 604/236 |
| 6,167,607 B1 | 1/2001 | Pryor | |
| 6,193,735 B1 | 2/2001 | Stevens | |
| 6,276,661 B1 * | 8/2001 | Laird | A61B 17/3462 604/167.03 |
| 6,398,755 B1 * | 6/2002 | Belef | A61M 25/0113 604/95.01 |
| 6,458,103 B1 | 10/2002 | Albert et al. | |
| 6,743,210 B2 | 6/2004 | Hart et al. | |
| 7,635,342 B2 | 12/2009 | Ferry et al. | |
| 7,766,894 B2 | 8/2010 | Weitzner et al. | |
| 7,887,549 B2 | 2/2011 | Wenderow et al. | |
| 7,896,845 B2 | 3/2011 | Ross et al. | |
| 7,922,693 B2 | 4/2011 | Reis | |
| 8,108,069 B2 | 1/2012 | Stahler et al. | |
| 8,202,252 B2 | 6/2012 | Ross | |
| 8,409,234 B2 | 4/2013 | Stahler et al. | |
| 8,425,465 B2 | 4/2013 | Nagano et al. | |
| 8,480,618 B2 | 7/2013 | Wenderow et al. | |
| 2002/0111585 A1 | 8/2002 | Lafontaine | |
| 2002/0111666 A1 | 8/2002 | Hart et al. | |
| 2002/0165537 A1 | 11/2002 | Kelley et al. | |
| 2003/0187369 A1 | 10/2003 | Lewis et al. | |
| 2004/0172008 A1 | 9/2004 | Layer | |
| 2005/0038456 A1 | 2/2005 | Vargas et al. | |
| 2005/0085789 A1 * | 4/2005 | Khan | A61M 39/0613 604/533 |
| 2006/0229587 A1 | 10/2006 | Beyar et al. | |
| 2008/0146942 A1 | 6/2008 | Dala-Krishna | |
| 2009/0024072 A1 * | 1/2009 | Criado | A61M 1/36 604/9 |
| 2009/0141263 A1 | 6/2009 | Cronin et al. | |
| 2009/0247944 A1 | 10/2009 | Kirschenman et al. | |
| 2009/0318799 A1 | 12/2009 | Wurmfeld et al. | |
| 2010/0010505 A1 | 1/2010 | Herlihy et al. | |
| 2010/0016800 A1 | 1/2010 | Rockrohr | |
| 2010/0036329 A1 | 2/2010 | Razack | |
| 2010/0069833 A1 | 3/2010 | Wenderow et al. | |
| 2010/0198158 A1 * | 8/2010 | Loewen | A61M 25/01 604/158 |
| 2010/0204646 A1 | 8/2010 | Plicchi et al. | |
| 2010/0298845 A1 | 11/2010 | Kidd et al. | |
| 2011/0028894 A1 | 2/2011 | Foley et al. | |
| 2011/0096331 A1 | 4/2011 | Jung | |
| 2011/0105954 A1 | 5/2011 | Cohen et al. | |
| 2011/0152777 A1 | 6/2011 | Bettuchi | |
| 2011/0264038 A1 | 10/2011 | Fujimoto et al. | |
| 2012/0071856 A1 | 3/2012 | Goldfarb et al. | |
| 2012/0179167 A1 | 7/2012 | Wenderow et al. | |
| 2014/0171863 A1 | 6/2014 | Blacker | |

FOREIGN PATENT DOCUMENTS

| | | |
|---|---|---|
| JP | 2012196444 | 10/2012 |
| WO | 9851364 | 11/1998 |
| WO | 2007098494 | 8/2007 |
| WO | 2009092059 | 7/2009 |
| WO | 2009120944 | 10/2009 |
| WO | 2009120945 | 10/2009 |
| WO | 2009137410 | 11/2009 |
| WO | 2010138499 | 12/2010 |
| WO | 2012037213 A1 | 3/2012 |
| WO | 2012088201 A2 | 6/2012 |
| WO | 2013043804 A1 | 3/2013 |
| WO | 2013043872 A1 | 3/2013 |

OTHER PUBLICATIONS

Office Action for JP 2016-523217; dated Aug. 28, 2018; office action and translation 6 pages.
Partial EESR for EP 20154304.8, dated Nov. 2, 2020.

* cited by examiner

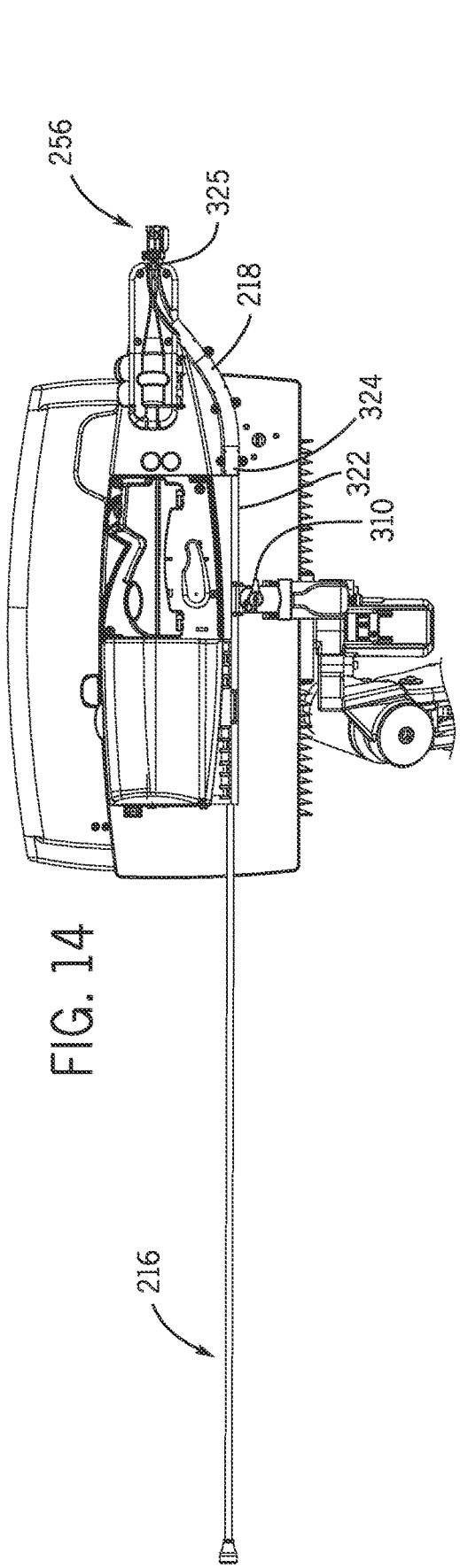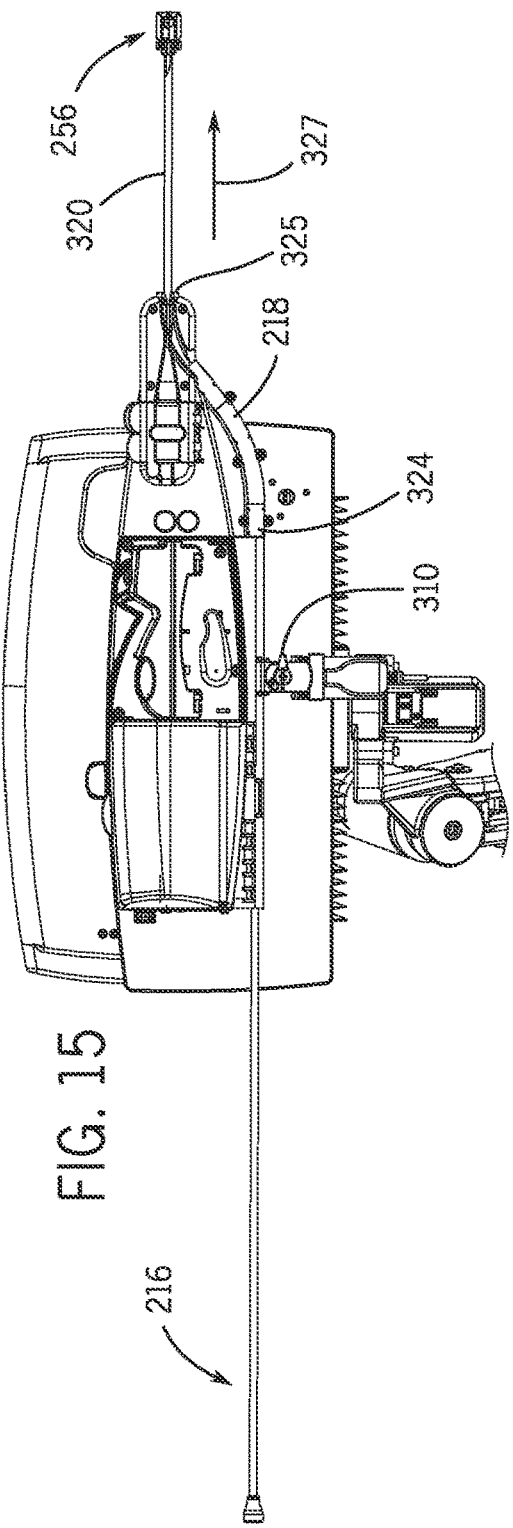

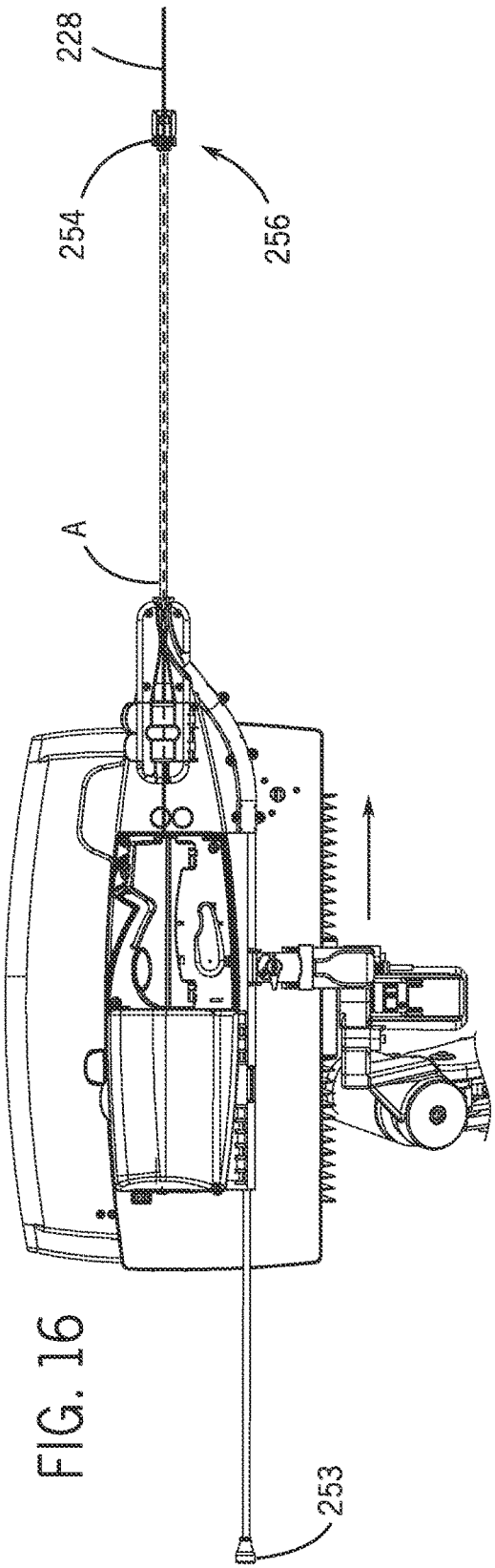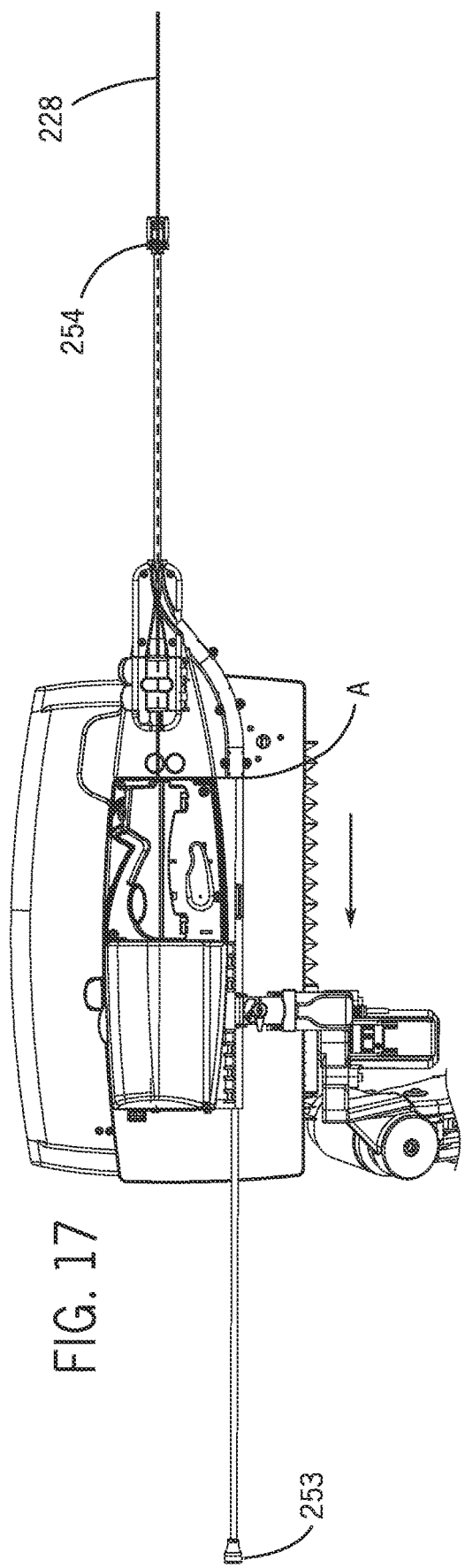

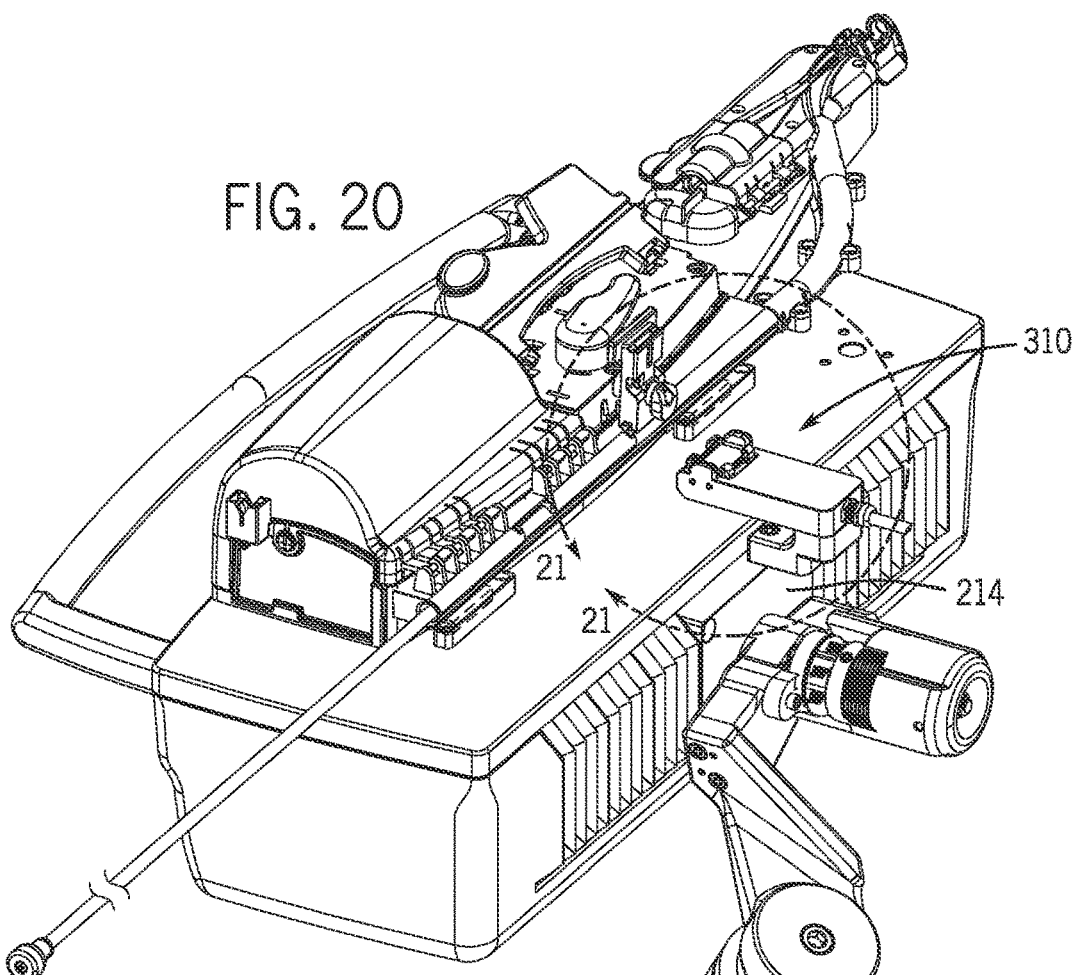
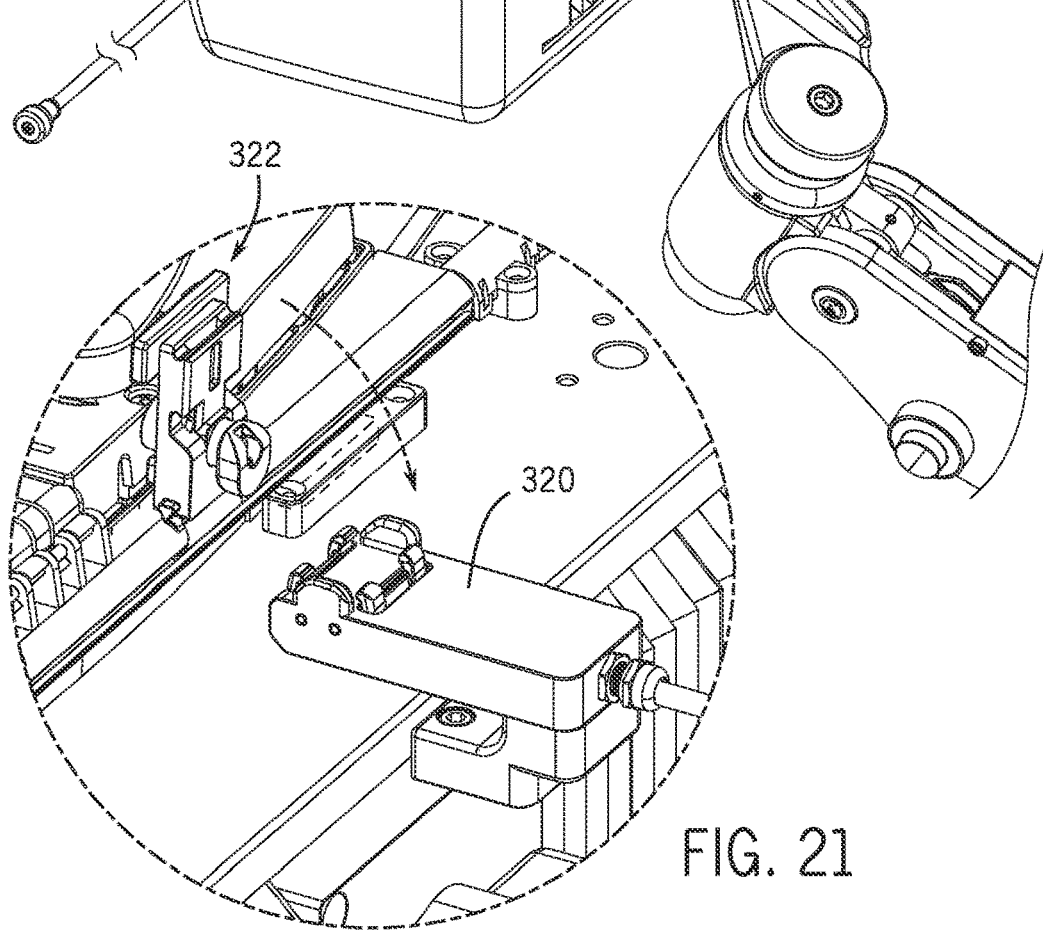

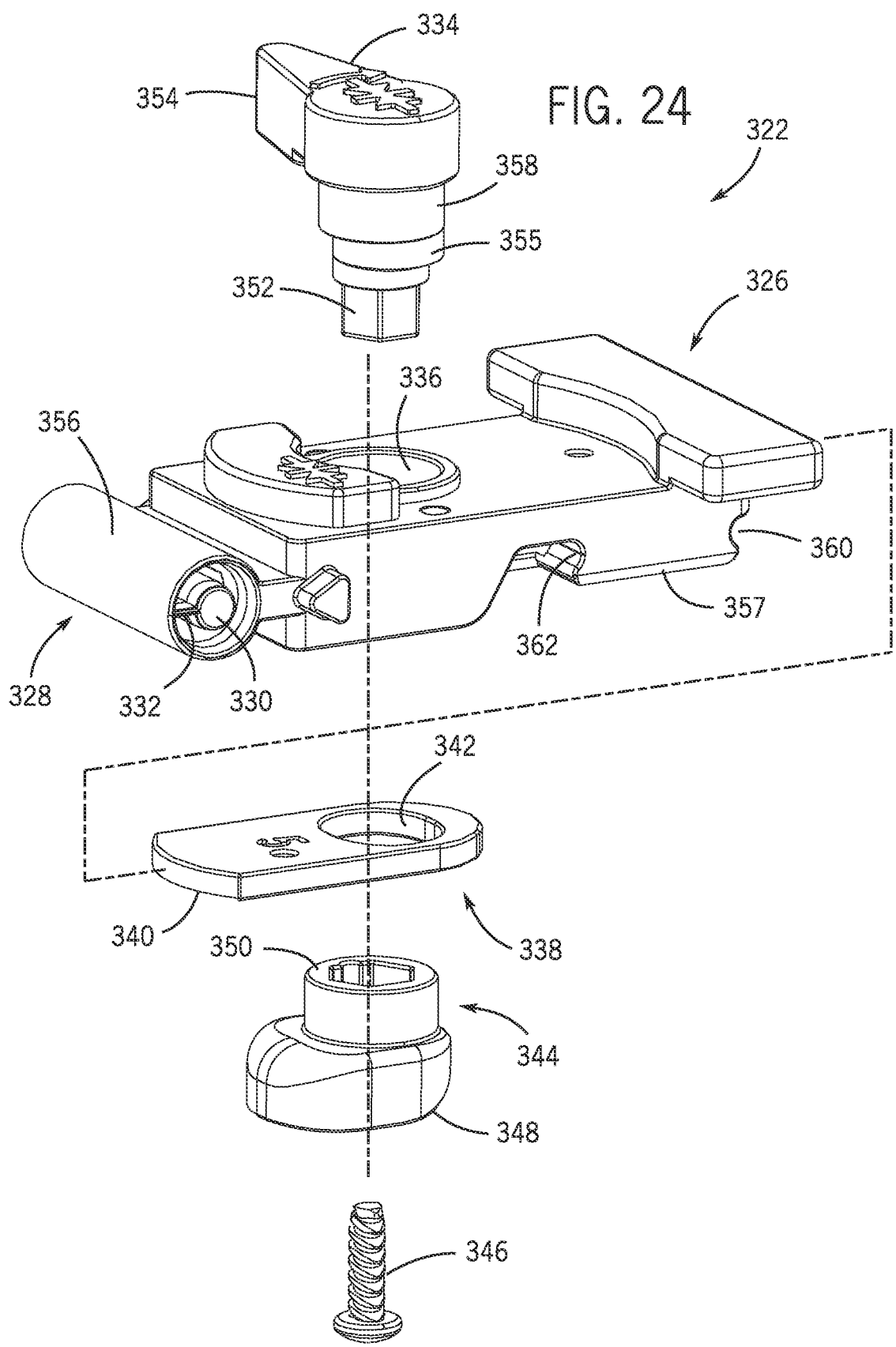

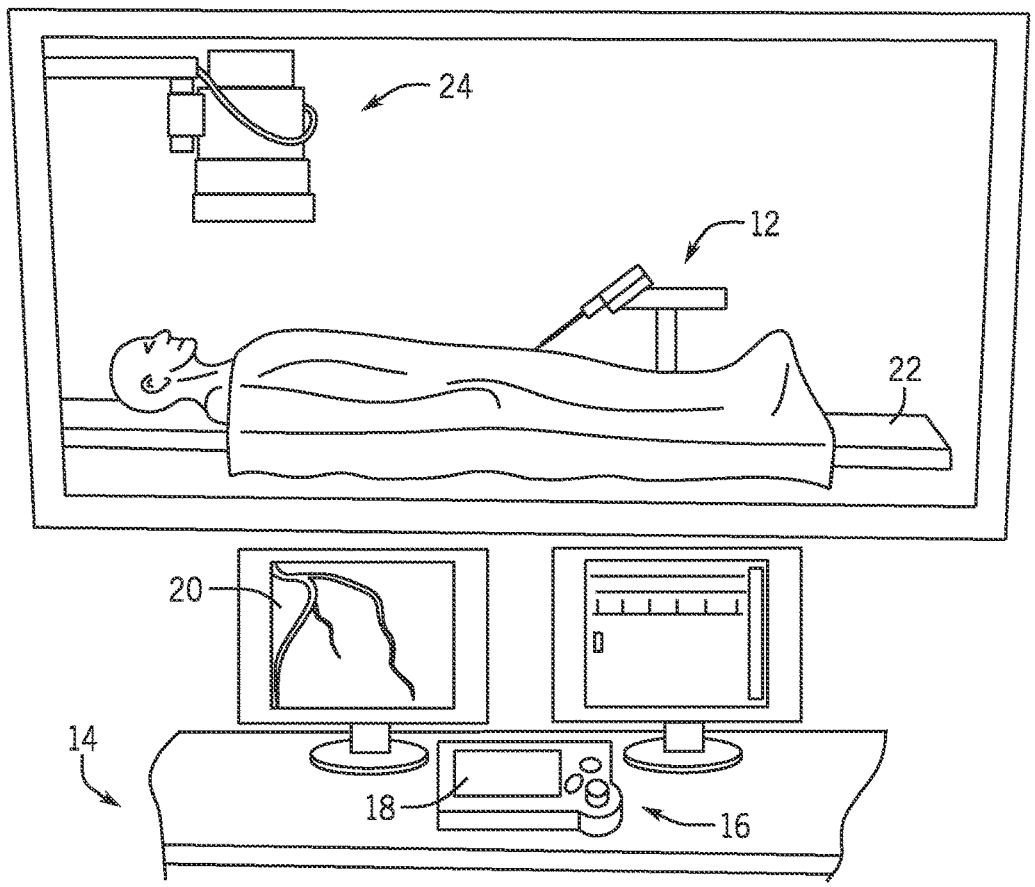
FIG. 27
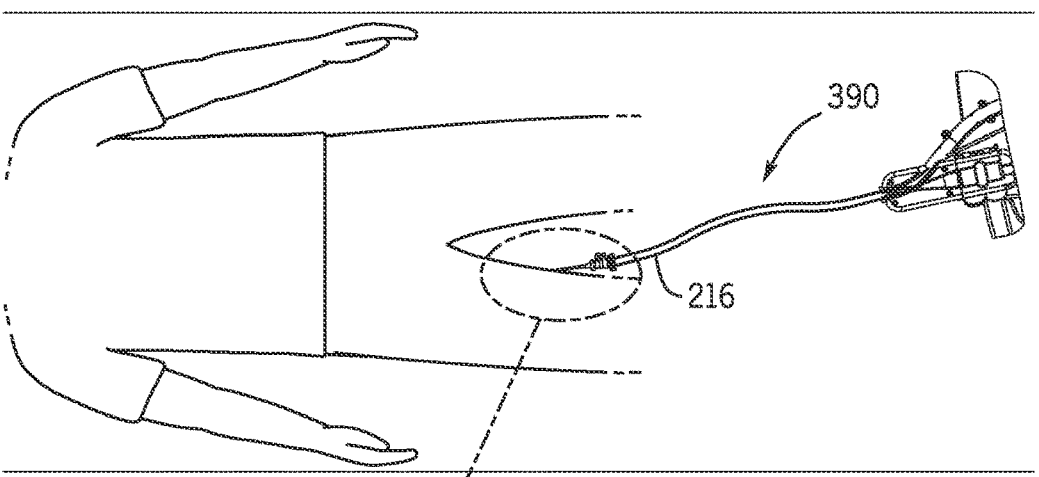
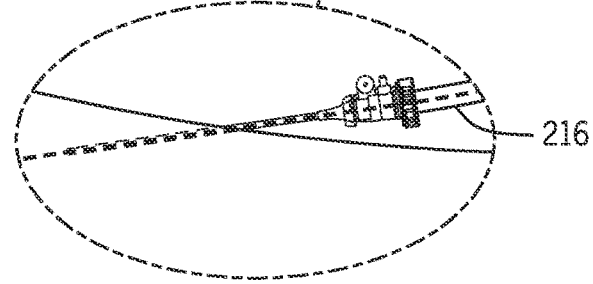
FIG. 28

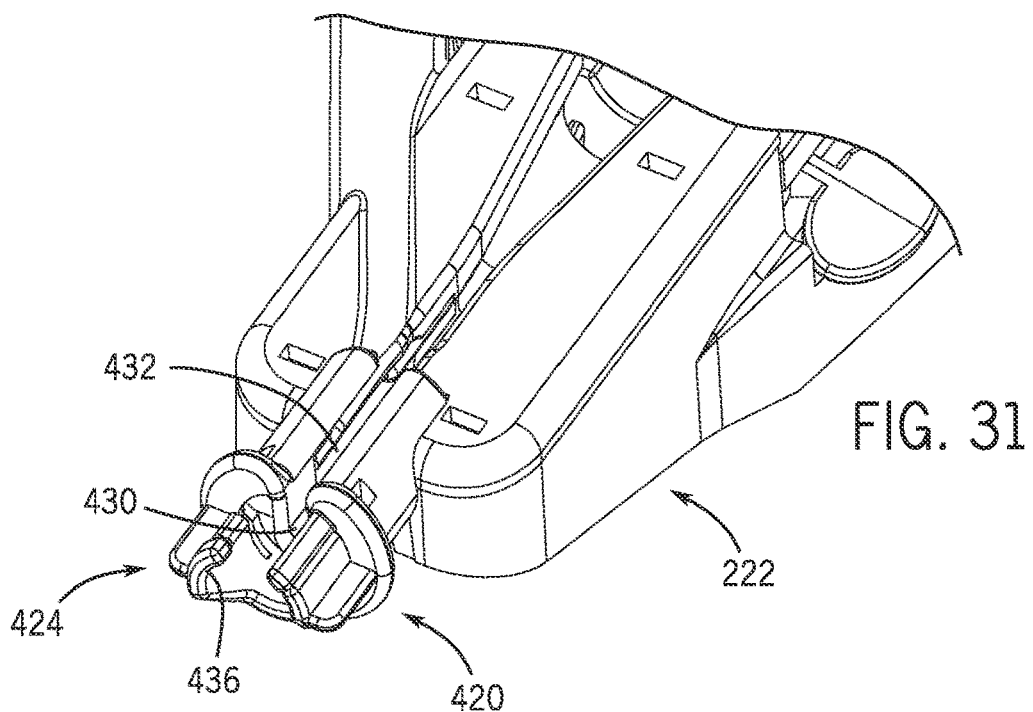
FIG. 31
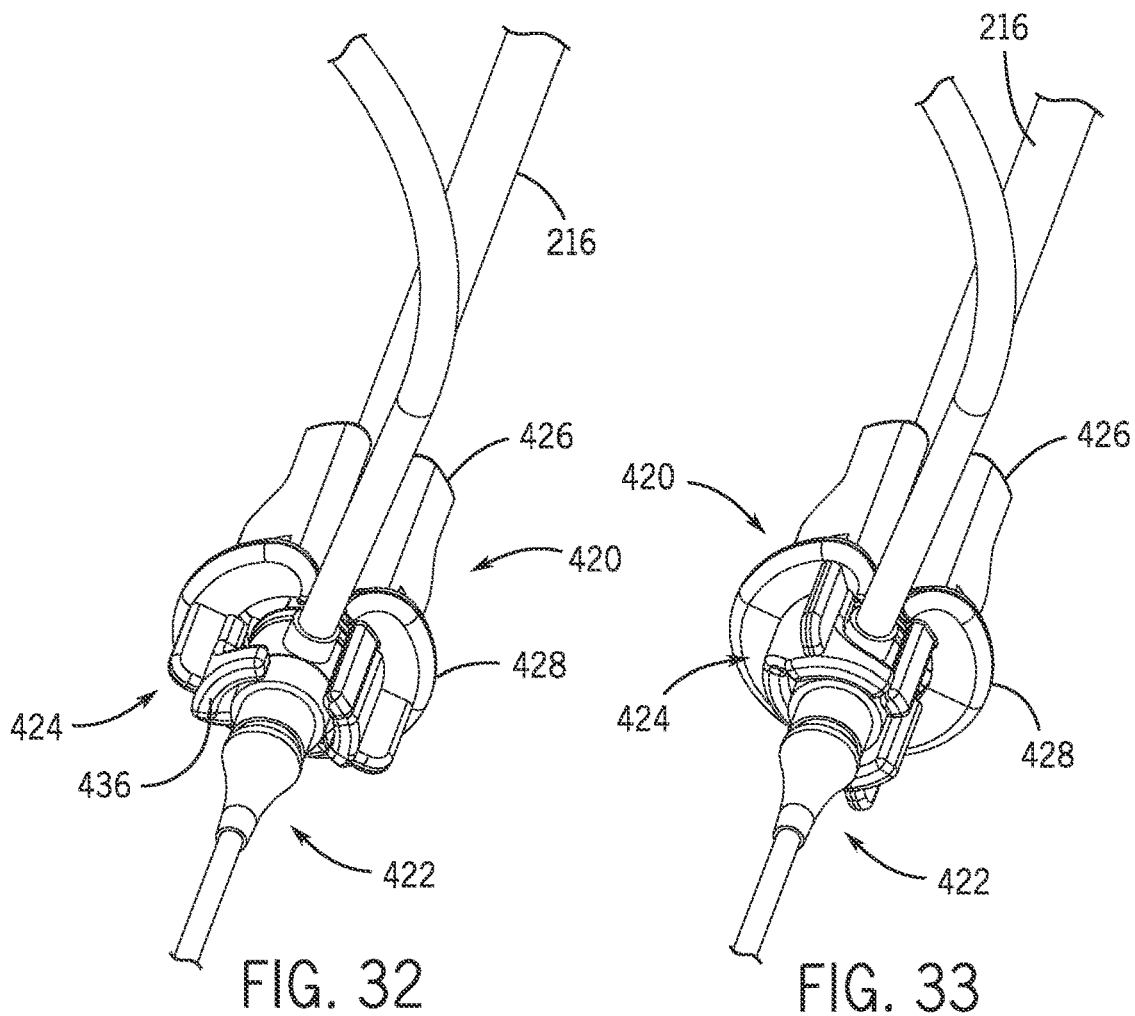
FIG. 32
FIG. 33

GUIDE CATHETER CONTROL FLEXIBLE TRACK

CROSS-REFERENCE TO RELATED PATENT APPLICATIONS

This application is a continuation of U.S. patent application Ser. No. 15/913,136, filed Mar. 6, 2018, which is a continuation of U.S. patent application Ser. No. 15/029,115, filed Apr. 13, 2016 entitled GUIDE CATHETER CONTROL FLEXIBLE TRACK which claims the benefit of PCT Patent Application No. PCT/US14/60664, filed Oct. 15, 2014, entitled GUIDE CATHETER CONTROL FLEXIBLE TRACK, U.S. Provisional Application No. 61/891,389, filed Oct. 15, 2013, entitled "GUIDE CATHETER CONTROL BENDABLE SUPPORT", and U.S. Provisional Application No. 61/952,872, filed Mar. 14, 2014, entitled "GUIDE CATHETER CONTROL BENDABLE SUPPORT", all of which are incorporated herein by reference in their entireties.

BACKGROUND OF THE INVENTION

The present application relates generally to the field of catheter systems for performing diagnostic and/or percutaneous coronary intervention procedures. The present application relates specifically to a guide catheter control in a robotic catheter system.

Vascular disease, and in particular cardiovascular disease, may be treated in a variety of ways. Surgery, such as cardiac bypass surgery, is one method for treating cardiovascular disease. However, under certain circumstances, vascular disease may be treated with a catheter based intervention procedure, such as angioplasty. Catheter based intervention procedures are generally considered less invasive than surgery.

During one type of intervention procedure, a guide catheter is inserted into a patient's femoral artery through an introducer and positioned proximate the coronary ostium of a patient's heart. A guide wire is inserted into the guide catheter typically through a hemostasis valve and maneuvered through the patient's arterial system until the guide wire reaches the site of the lesion. A working catheter is then moved along the guide wire until the working catheter such as a balloon and stent are positioned proximate the lesion to open a blockage to allow for an increased flow of blood proximate the lesion. In addition to cardiovascular disease, other diseases may be treated with catheterization procedures.

SUMMARY

In accordance with an embodiment, a system for controlling a hemostasis valve includes a hemostasis valve having a body portion having a proximal end, a distal end and a lumen extending between the proximal end and the distal end, at least one valve positioned in the proximal end of the body portion and an engagement member operatively coupled to the at least one valve. The system further includes a first drive member coupled to the engagement member and a controller coupled to the first drive member, the controller configured to control the first drive member to impart movement to the engagement member to open and close the at least one valve In accordance with another embodiment, a system for controlling a hemostasis valve includes a hemostasis valve having a body portion having a proximal end, a distal end and a lumen extending between the proximal end and the distal end, at least one valve positioned in the proximal end of the body portion and an engagement member operatively coupled to the at least one valve. The system further includes a sensor configured to detect blood flow and a controller coupled to the sensor and the engagement member, the controller configured to control the engagement member to operate the at least one valve based on the blood flow detected by the sensor.

In accordance with another embodiment, a system for controlling a hemostasis valve incudes a hemostasis valve having a body portion having a proximal end, a distal end and a lumen extending between the proximal end and the distal end, at least one valve positioned in the proximal end of the body portion and an engagement member operatively coupled to the at least one valve. The system further incudes a sensor configured to detect a frictional force required to move an elongated medical device and a controller coupled to the sensor and the engagement member, the controller configured to control the engagement member to operate the at least one valve based on the detected frictional force.

BRIEF DESCRIPTION OF THE DRAWINGS

This application will become more fully understood from the following detailed description, taken in conjunction with the accompanying figures, wherein like reference numerals refer to like elements in which:

FIG. 14 is a top plan view of the robotic catheter system with the flexible track in the fully retracted position.

FIG. 15 is a top plan view of the robotic catheter system with the flexible track in an extended position.

FIG. 16 is a top plan view of the robotic catheter system with the robotic drive in a first position.

FIG. 17 is a top plan view of the robotic catheter system with the robotic drive in a second extended position.

FIG. 20 is a rear isometric view of the robotic catheter system with the cassette secured to the robotic drive base with the locking track clamp in the disengaged position.

FIG. 21 is a close up view of the locking track clamp taken generally along lines 21-21 of FIG. 20.

FIG. 24 is an exploded view of a portion of the locking track clamp.

FIG. 27 is a schematic view of the robotic catheter system with a remote control station.

FIG. 28 is illustration of robotic catheter system with the guide catheter engaged with a patient.

FIG. 31 is an isometric view of a sheath clip.

FIG. 32 is an isometric view of the sheath clip of FIG. 31 with an introducer.

FIG. 33 is an isometric view of the sheath clip of FIG. 31 with an introducer connected to the sheath clip.

DETAILED DESCRIPTION OF THE PREFERRED EMBODIMENTS

Figure 1:
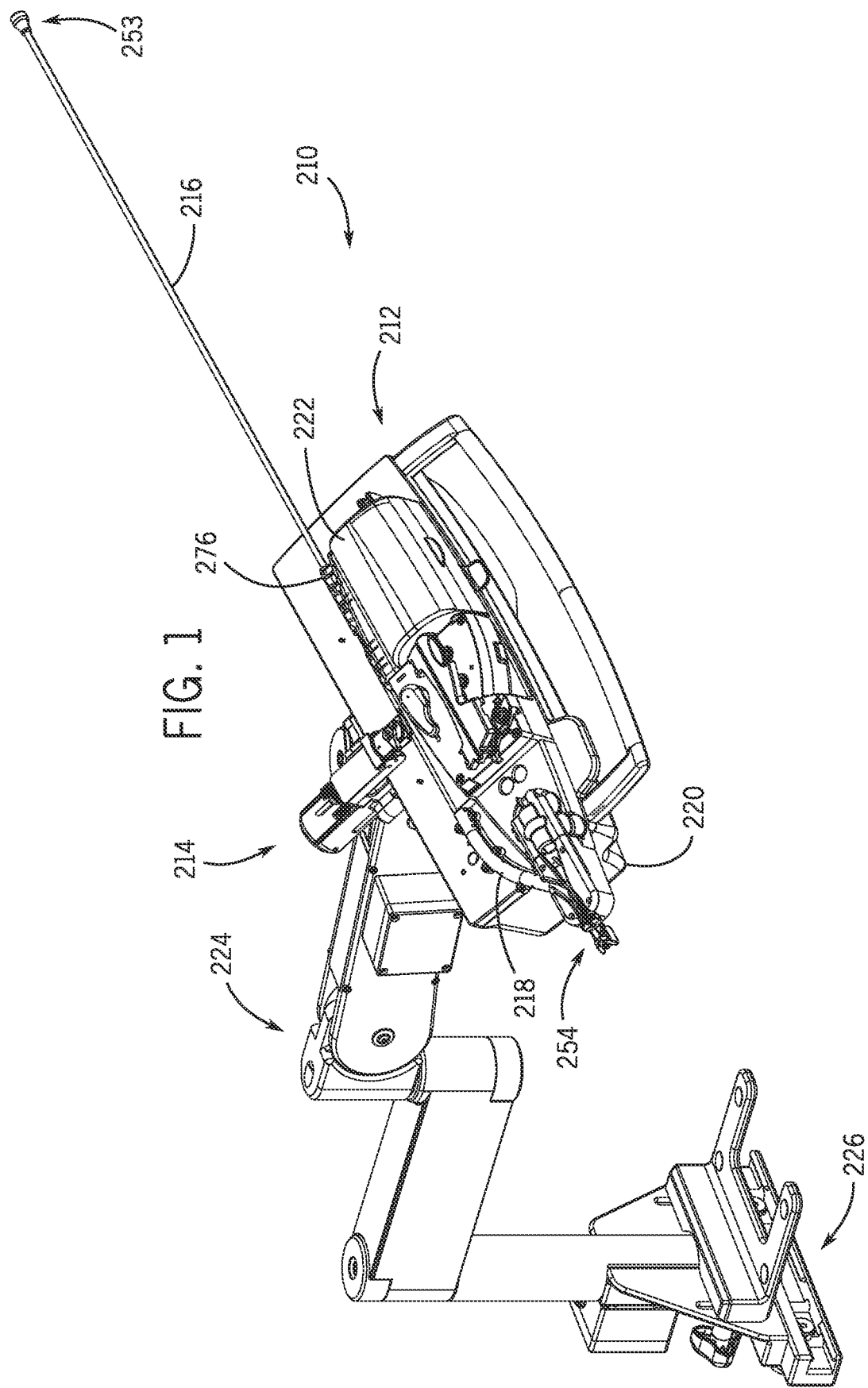
FIG. 1 is an isometric view of a robotic catheter system.

Referring to FIG. 1 a robotic catheter system 210 includes a robotic mechanism 212 robotically moving an elongated medical device. The robotic mechanism 212 is movable relative to a base 214. A flexible track 216 is movable along a rigid guide track 218 having a non-linear portion. Referring to FIG. 16 flexible track 216 includes a proximal end 253 and a distal end 254.

As described in more detail herein, flexible track 216 supports an elongated medical device such as a guide catheter so that the guide catheter can be advanced into the patient without buckling.

As used herein the direction distal is the direction toward the patient and the direction proximal is the direction away from the patient. The term up and upper refers to the general direction away from the direction of gravity and the term bottom, lower and down refers to the general direction of gravity. The term front refers to the side of the robotic mechanism that faces a user and away from the articulating arm. The term rear refers to the side of the robotic mechanism that is closest to the articulating arm. The term inwardly refers to the inner portion of a feature. The term outwardly refers to the outward portion of a feature.

Robotic mechanism 212 includes a robotic drive base 220 movable relative to base 214 and a cassette 222 that is operatively secured to robotic drive base 220. In one embodiment cassette 222 includes structure that defines support rigid guide 218. In one embodiment base 214 alone or in combination with cassette 222 defines rigid guide 218.

In one embodiment base 214 is secured to an articulating arm 224 that allows a user to position robotic mechanism 212 proximate a patient. In one embodiment base 214 is the distal portion of the articulating arm 224. Articulating arm 224 is secured to a patient bed by a rail clamp or a bed clamp 226. In this manner base 214 is secured to a patient bed. By manipulation of articulated arm 224 the base 214 is placed in a fixed location relative to a patient that lies upon the patient bed. The arms of articulated arm 224 can be fixed once the desired location of robotic mechanism 212 is set relative to the patient.

Figure 2:
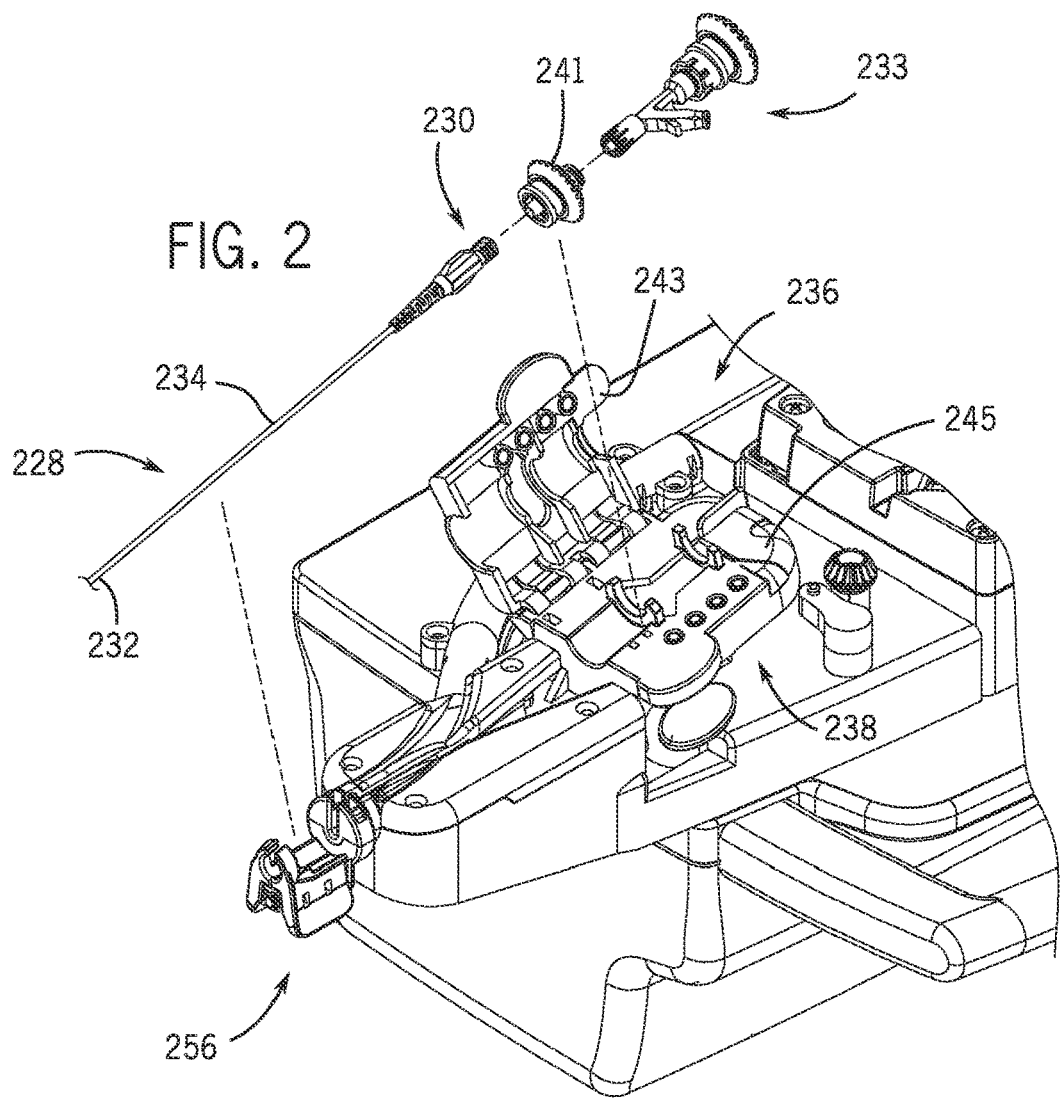
FIG. 2 is top isometric view of a front portion of the robotic catheter system of FIG. 1 with an exploded view of a guide catheter and Y-connector.

Referring to FIG. 2 an elongated medical device such as a guide catheter 228 is operatively secured to robotic mechanism 212 through cassette 222. Guide catheter 228 includes a proximal end 230, an opposing distal end 232, and an intermediate portion 234 extending between the proximal end 230 and distal end 232. In one embodiment proximal end 230 of guide catheter 228 is operatively secured to a Y-connector 233 and Y-connector engagement mechanism 236. In one embodiment Y-connector 233 is a hemostasis valve that is secured to cassette 222 by a Y-connector engagement mechanism 236 including a Y-connector base 238 that is part of cassette 222 and an enclosure member 244 including a lid 243 and a support member 245. Y-connector base 238 includes a guide catheter drive mechanism 240 located in the cassette 222 which in turn is operatively connected to robotic base 220. Guide catheter drive mechanism 240 includes a drive mechanism that operatively engages and rotates guide catheter 228 along its longitudinal axis correction about its longitudinal axis based on commands provided by a remote control center.

Figure 3:
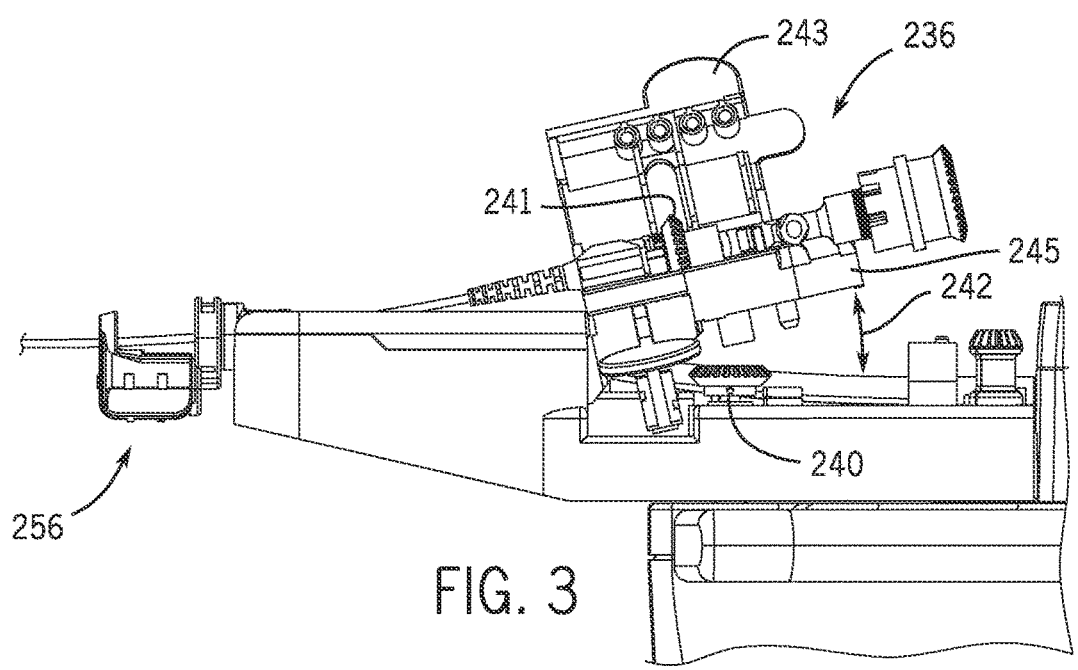
FIG. 3 is a side front view of the front portion of the robotic catheter system of FIG. 2 with the guide catheter positioned within a Y-connector support in a raised position.
Figure 4:
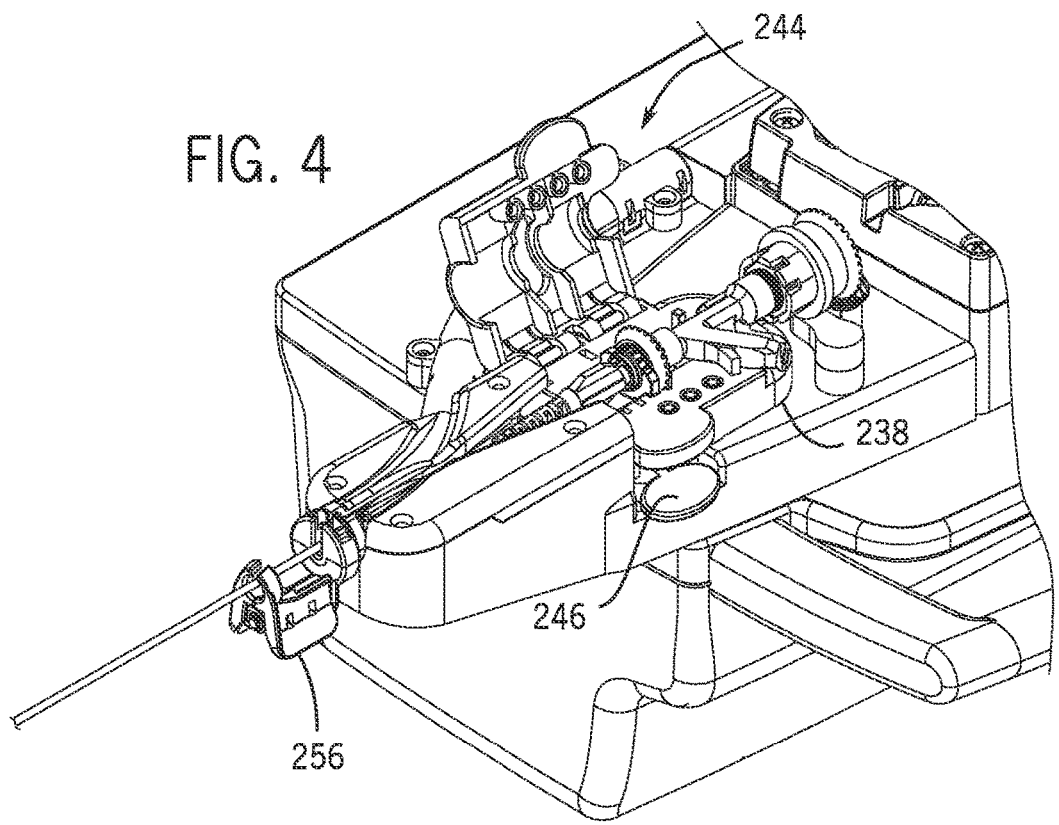
FIG. 4 is an isometric view of the portion of the system of FIG. 2 with the Y-connector and support in a lowered position with the Y-connector support cover in the raised position.

Referring to FIG. 3, Y connector enclosure 244 pivots to a raised install position to provide easy installation of guide catheter 228 and Y-connector 233. Referring to FIG. 4, the Y-connector enclosure 244 pivots along vector 242 from the raised position to an in-use operational lower position. In one embodiment guide catheter drive mechanism 240 interacts with a gear 241 on a rotating luer lock connector secured to proximal end 230 of guide catheter 228 to robotically rotate guide catheter 228 about its longitudinal axis. The operation of a Y-connector holder and drive mechanism 236 to robotically rotate guide catheter 228 about its longitudinal axis is described in published US Patent Application No. US 2014/0171863 A1 entitled Hemostasis Valve for Guide Catheter Control which is incorporated herein by reference in its entirety. The robotic control of the Y-connector hemostasis valve 233 will be discussed in further detail below.

Referring to FIG. 4 and FIG. 6, Y connector holder 238 includes a cover 244 which pivots from an open position to a closed position. Y connector holder 238 is releasably engaged to a portion of cassette 222 by a release button 246. Movement of lever 246 allows Y connector holder 238 to be pivoted from the operational lower position to the raised position to load guide catheter 228 and Y-connector 233.

Figure 5:
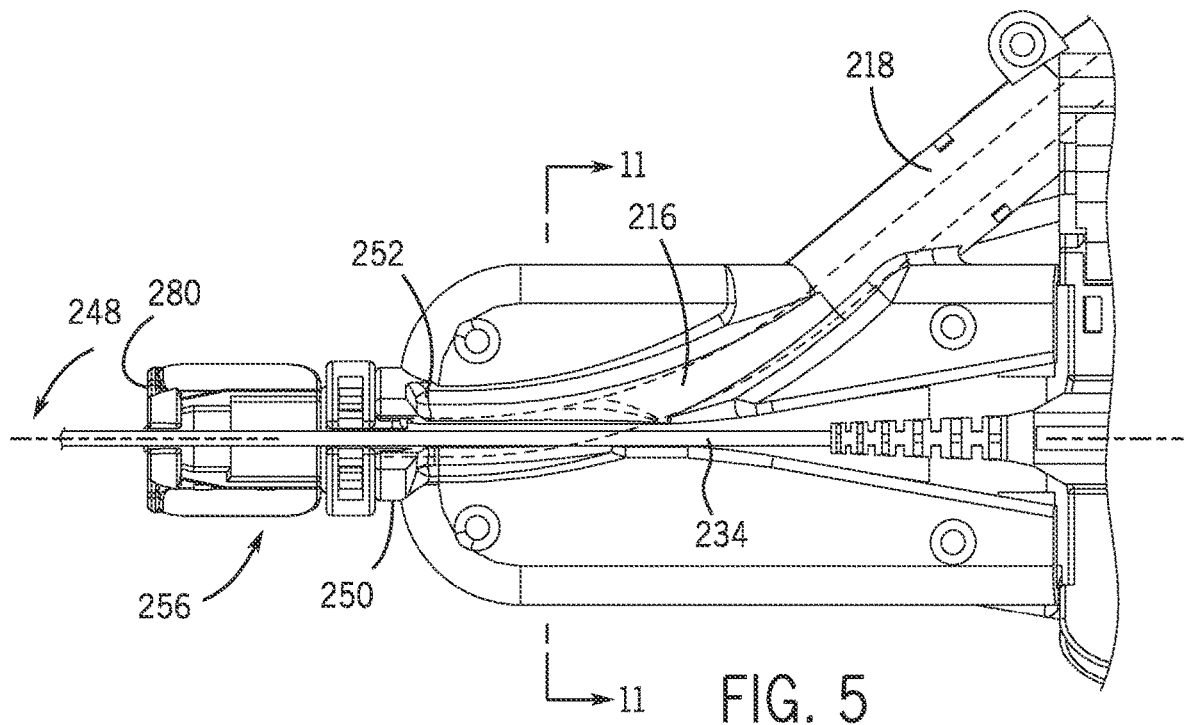
FIG. 5 is a top plan view of the front portion of the robotic catheter system of FIG. 2 with the guide catheter in the engaged position.

Referring to FIG. 5 the relationship between guide catheter 228, rigid guide 218, and flexible track 216 will be described. Guide catheter 228 maintains a linear position along its longitudinal axis 248 within cassette 222 and for at least a certain distance distal cassette 222. In one embodiment longitudinal axis 248 corresponds to the longitudinal axis of cassette 222.

During a medical procedure such as a percutaneous coronary intervention (PCI) guide catheter 228 is used to guide other elongated medical devices such as a guide wire and balloon stent catheter into a patient to conduct an exploratory diagnosis or to treat a stenosis within a patient's vasculature system. In one such procedure the distal end 232 of the guide catheter 228 is seated within the ostium of a patient's heart. Robotic mechanism 212 drives a guide wire and/or a working catheter such as a balloon stent catheter in and out of a patient. The guide wire and working catheter are driven in within the guide catheter 228 between the distal end of the robotic mechanism 212 and the patient. In one embodiment longitudinal axis 248 is the axis about which cassette 222 causes rotation of a guide wire and the axis along which cassette 222 drives the guide wire along its longitudinal axis and drives a working catheter such as a balloon stent catheter along its longitudinal axis. In one embodiment the robotic drive system is of the type described in U.S. Pat. No. 7,887,549 entitled Catheter System and incorporated herein by reference in its entirety.

Figure 7:
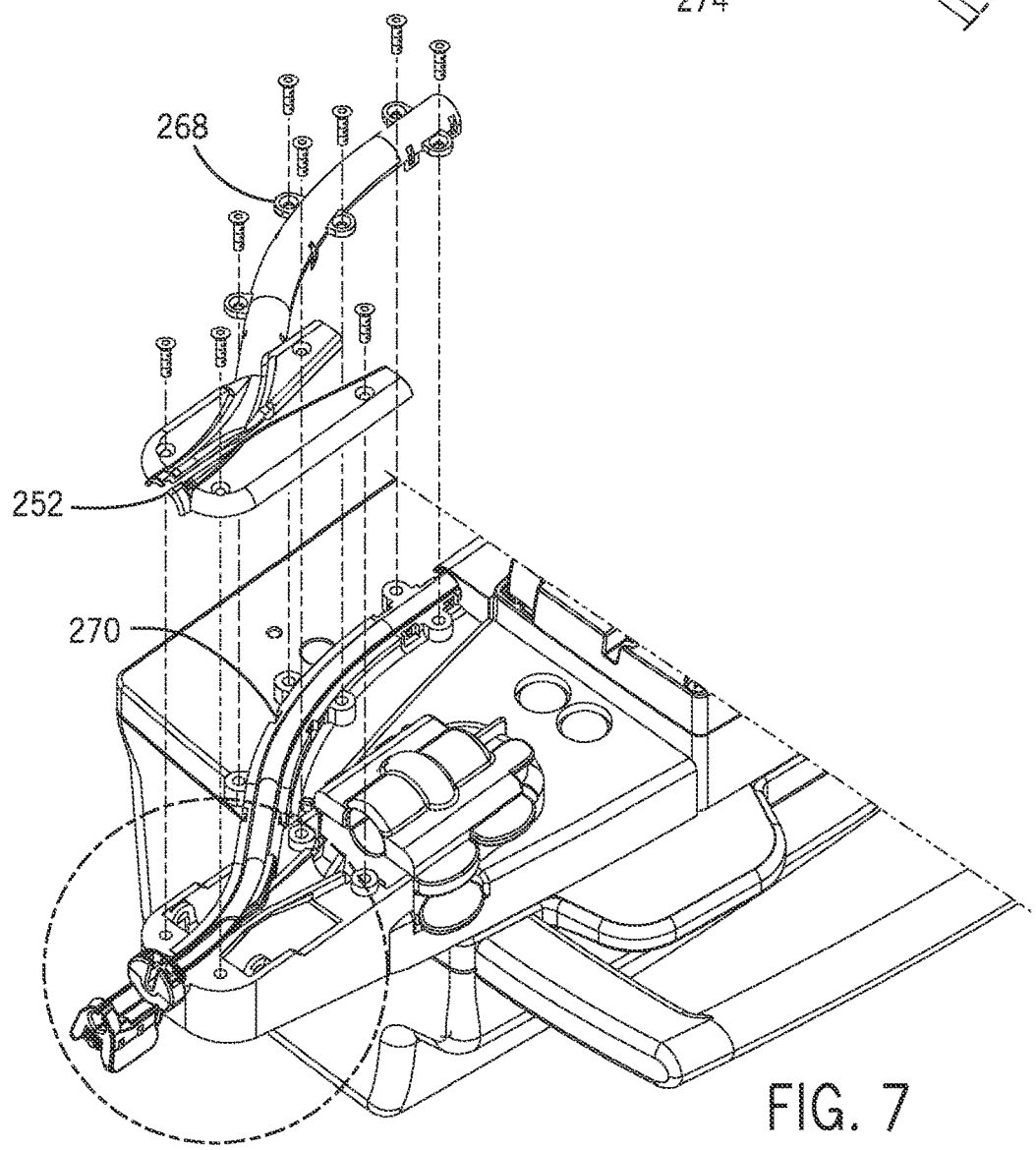
FIG. 7 is an exploded view of the arcuate portion of the rigid guide and front of the robotic catheter system.
Figure 9:
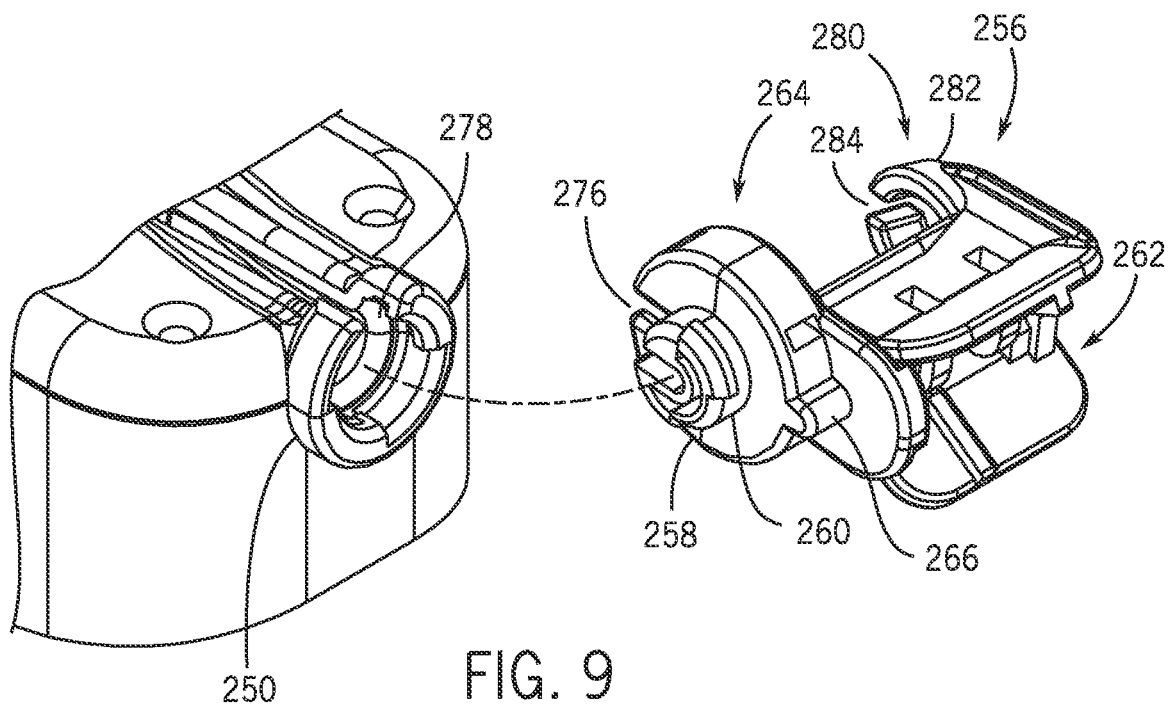
FIG. 9 is an exploded view of the sheath clip and distal end of the rigid guide.

Referring to FIGS. 5, 7 and 9 a collar 250 is formed at the distal end of rigid guide 218. Collar 250 includes a vertically extending opening 278 through which guide catheter 228 is loaded into flexible track 216.

The terminal end 254 of flexible track 216 is secured to a sheath clip 256 which is releasably connected to cassette 222. Flexible track 246 includes a collar 250 secured to a terminal distal end 252. Referring to FIG. 9 in one embodiment a sheath clip 256 includes a proximal end 258 including an attachment portion 260. The distal end 254 of flexible track 216 is secured to attachment portion 260. Sheath clip 256 includes a grasping portion 262 that allows a user to manipulate sheath clip 256 and flexible track 216. Intermediate the grip portion 262 and the flexible track attachment portion 260 is a collar engagement portion 264. Collar engagement portion 264 and includes a guiding locating member 266 configured to position sheath clip 256 within collar 250.

Referring to FIG. 7 rigid guide 218 includes a top member 268 and a bottom channel member 270. Top member 268 and bottom channel member 270 when secured together with a plurality of fasteners or other fastening mechanism forms an interior channel 272 through which flexible track 216 moves relative to rigid guide 218.

Figure 8:
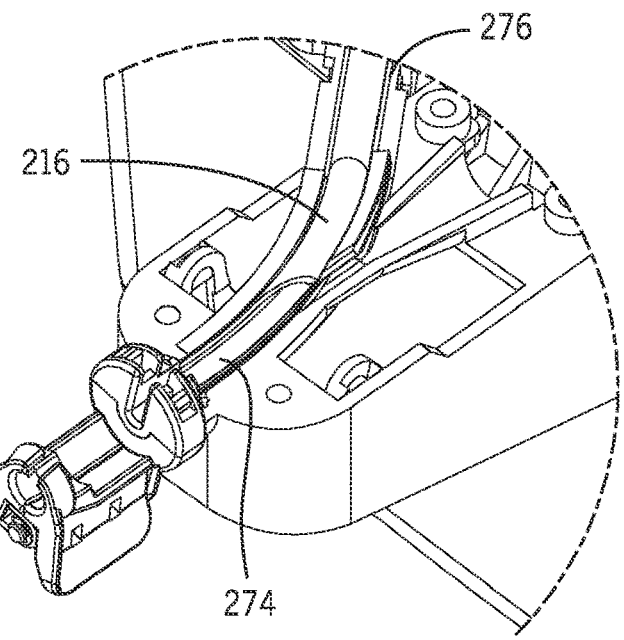
FIG. 8 is a close up of the sheath clip, flexible track and rigid support of FIG. 7.

Referring to FIG. 8 flexible track 216 includes an opening 274 located adjacent to the terminal end 254 of flexible track 216 a predetermined distance toward proximal end of flexible track 216. When distal end 254 of flexible track 216 is positioned adjacent collar 250 opening 274 extends from collar 250 toward Y-connector holder a distance sufficient such that opening 274 extends from collar 250 to the area in which rigid guide 218 begins an arcuate path away from longitudinal axis 248. In one embodiment arcuate path forms an s-curve having at least one point of inflection along the arcuate path. As discussed below opening 274 provides a path for guide catheter 228 to be placed into the hollow cavity of flexible track directly from a position above longitudinal axis. In this manner guide catheter 228 may be placed within flexible track 216 proximate opening 274 while guide catheter 228 is linear. Stated another way in one embodiment guide catheter 228 is in a straight line when the guide catheter 228 is inserted through opening 274. In one embodiment opening 274 extends 90 degrees about the opening of the terminal end 254 of flexible track 216. Opening 274 tapers to a slit 286 that extends substantially the entire length of flexible track 216. In one embodiment slit 286 extends from opening 274 a distance sufficient to allow guide catheter 228 to enter and exit an interior portion of flexible track 216 throughout the entire intended operation of robotic catheter system. Opening 274 is defined by a pair of substantially parallel cut lines 288, 290 in the outer surface of flexible track 216. Opening 274 is further defined by a tapered region 294 with an arcuate line 296 extending from cut line 288 toward slit 286. In one embodiment flexible track 216 has sufficient rigidity to maintain slit 286 in the open position, that is the two portions of the outer surface of flexible track 216 that define slit 286 remain separated during movement of the flexible track 216 as described herein and do not collapse onto one another such that no opening is present. In one embodiment slit 286 collapses during certain portions of flexible track 216 as it moves through certain sections of rigid guide 218. In one embodiment slit 286 collapses that is the two edges that define the slit are in contact with one another except in the area in which guide catheter 228 enters and exits flexible track 218. The edges defining the slit are forced apart by extension member 298 in the region where the longitudinal axis 248 is coincident with the portion of rigid guide that begins the non-linear arcuate portion.

Referring to FIG. 1 the distal end of flexible track 216 is fed into the channel of rigid guide 218 through its proximal opening 276. Rigid guide 218 includes a linear portion beginning at proximal opening 276 and a non-linear portion defined by cover 268 and base 270. In one embodiment the non-linear portion is an arcuate portion having at least one point of inflection. Flexible track 216 is initially positioned within rigid guide 218 by feeding distal end 254 of flexible track 218 into proximal opening 276 of rigid guide 218 until the distal end 254 of flexible track 216 extends beyond collar 250 of rigid guide 218. The distal end 254 of flexible track 216 is operatively connected to member 258 of sheath clip 256. Sheath clip 258 is positioned within collar 250 such that member 266 is positioned within a corresponding mating groove in collar 250. Sheath clip 256 is positioned in a first load position with channel opening 276 of sheath clip 258 aligned with opening 278 of collar 250.

Flexible track 216 is rotated by a technician or operator within rigid guide 218 such that opening 274 faces in an upwardly direction. Stated another way opening 274 of flexible track 216 is secured to sheath clip 256 in a manner such that when sheath clip 256 is engaged with collar 250 opening 276 of sheath clip 256 is aligned with opening 278 of collar 250 which is also aligned with opening 274 of flexible track 216.

Figure 10:
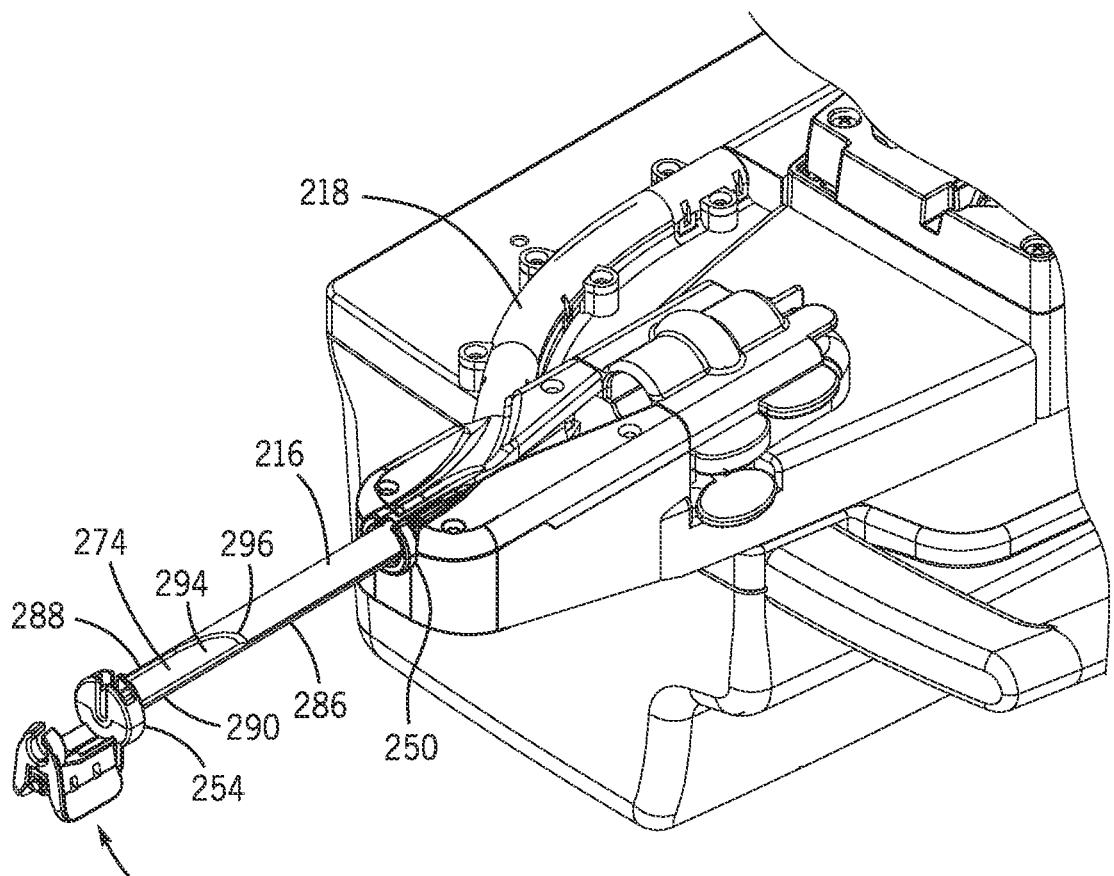
FIG. 10 is an isometric view of the front portion of the robotic catheter system with the flexible track in an extended position.

Referring to FIG. 10 flexible track 216 is secured to sheath clip 256 with a portion of flexible track 216 extending beyond collar 250 in the distal position. The extension of the distal end 254 of flexible track 216 allows for easy insertion of flexible track 216 to sheath clip 256. Since flexible track 216 is formed of a flexible material having a modulus of elasticity that is less than the modulus of elasticity of the rigid guide material, flexible track 216 moves along the curved non-lineal portion of channel defined by rigid guide 218. Note that the modulus of elasticity of flexible track 216 is below a value in which flexible track 216 will fracture or break by movement along the non-linear portion of rigid guide 218. In one embodiment flexible track 216 is formed of a polytetrafluoroethylene PTFE material. Sheath clip 256 along with the terminal end 254 of flexible track 216 is moved adjacent to collar 250. Sheath clip 256 along with flexible track 216 is rotated to such that the opening 276 of sheath clip 256 is alignment with opening 278 of collar 250 defining the guide catheter installation position. As discussed below in one embodiment a sheath clip 420 is configured to be received within cassette 222 in the proper install orientation.

Referring to FIG. 5 guide catheter 228 is positioned within opening 274 of flexible track 216 through opening 278 of collar 250 and through opening 276 of sheath clip 256. Referring to FIG. 5 and FIG. 9 the distal end 280 of sheath clip 256 includes a collar 282 having an opening 284. Guide catheter 228 in the installation position extends into flexible track 216 through opening 274, through opening 278 of collar 250 and through openings 276, 284 of sheath clip 256. In this installation position guide catheter 228 maintains a straight and linear orientation along its longitudinal axis 248 from Y-connector holder 236 through the distal end of sheath clip 256.

Figure 11:
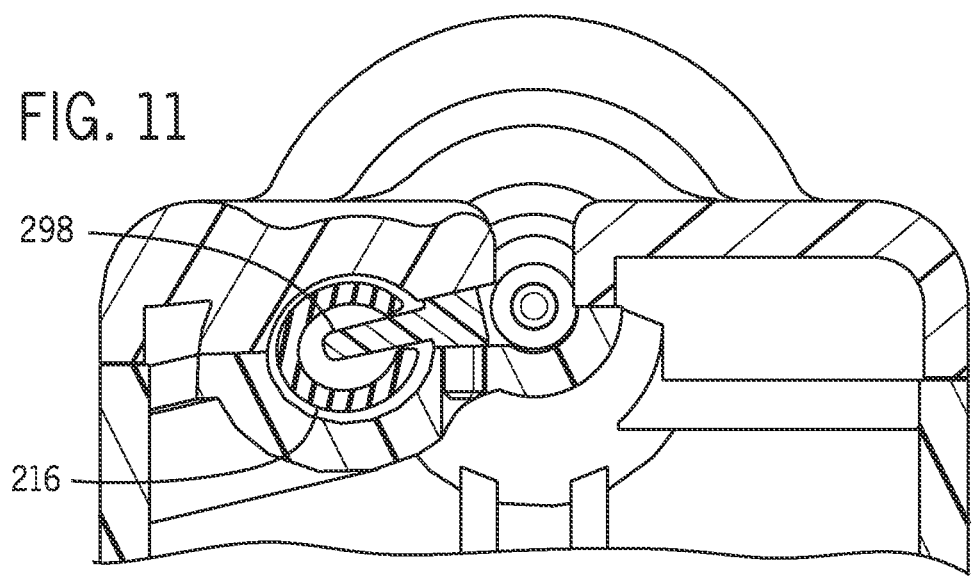
FIG. 11 is cross-sectional view of the front portion of the robotic catheter system taken generally along line 11-11 of FIG. 5 showing an extension member protruding into a slit of the flexible track.

Referring to FIG. 11, rigid guide 218 includes an extension member 298 that extends into the channel defined by the outer walls of rigid guide 218. Extension member 298 is received into the inner channel of flexible track 218 through slit 286. Extension member 298 is positioned proximate the distal end 300 of the arcuate portion of rigid guide 218. Extension member 298 has a thickness that is equal to or greater than the opening defined by slit 286 to ensure that the edges of flexible track 216 that define the slit remains separated so that guide catheter 228 can extend into the channel portion of flexible track 216 through the slit. In one embodiment the thickness of extension member 298 is greater than the opening defined by the slit and the diameter of the guide catheter 228. In this manner the opening defined by the slit 286 is increased at and closely adjacent to the extension member allowing for insertion and removal a portion of guide catheter 228. In one embodiment the opening defined by the slit is less than the diameter of the guide catheter 228 which assists in maintaining the distal portion of the guide catheter within the channel of the flexible track 216 during operation of the robotic catheter system.

Figure 6A:
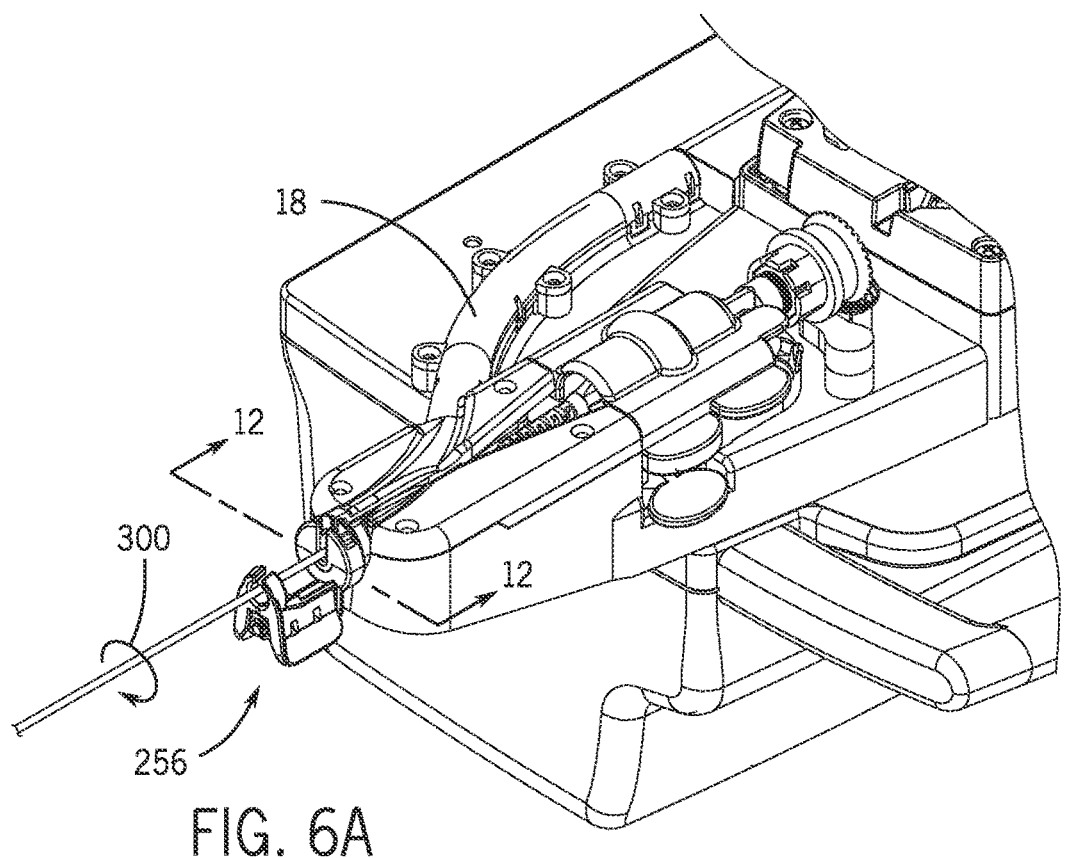
FIG. 6A is an isometric view of the robotic catheter system with the sheath clip in an install position.
Figure 12:
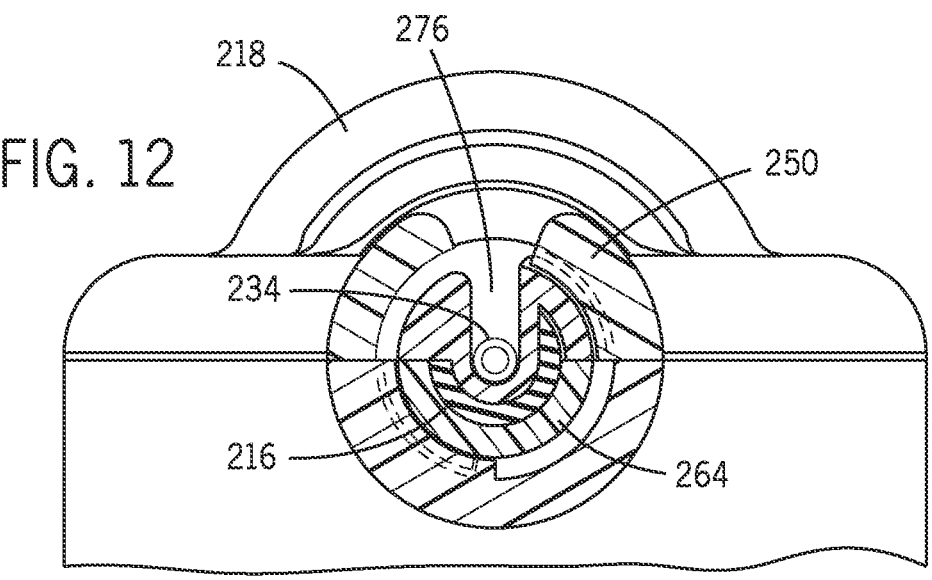
FIG. 12 is a cross-sectional view of the front portion of the robotic catheter system taken generally along lines 12-12 of FIG. 6A with the sheath clip in an in-load position.

Referring to FIG. 6A, and FIG. 12, sheath clip 256 is placed in an installation position with opening 276 in the upward direction. Stated another way opening 276 is formed by a channel in sheath clip 256 defining an opening that is accessed from the upward direction. This orientation allows guide catheter 228 to be positioned within the channel of sheath clip 256 and opening 274 of flexible track 216 in the same orientation that guide catheter is secured to cassette 222. In this orientation guide catheter 228 can be placed into the channel of flexible track 216 through openings 276 and 284 of sheath clip 256 and through opening 274 of flexible track 216.

Figure 6B:
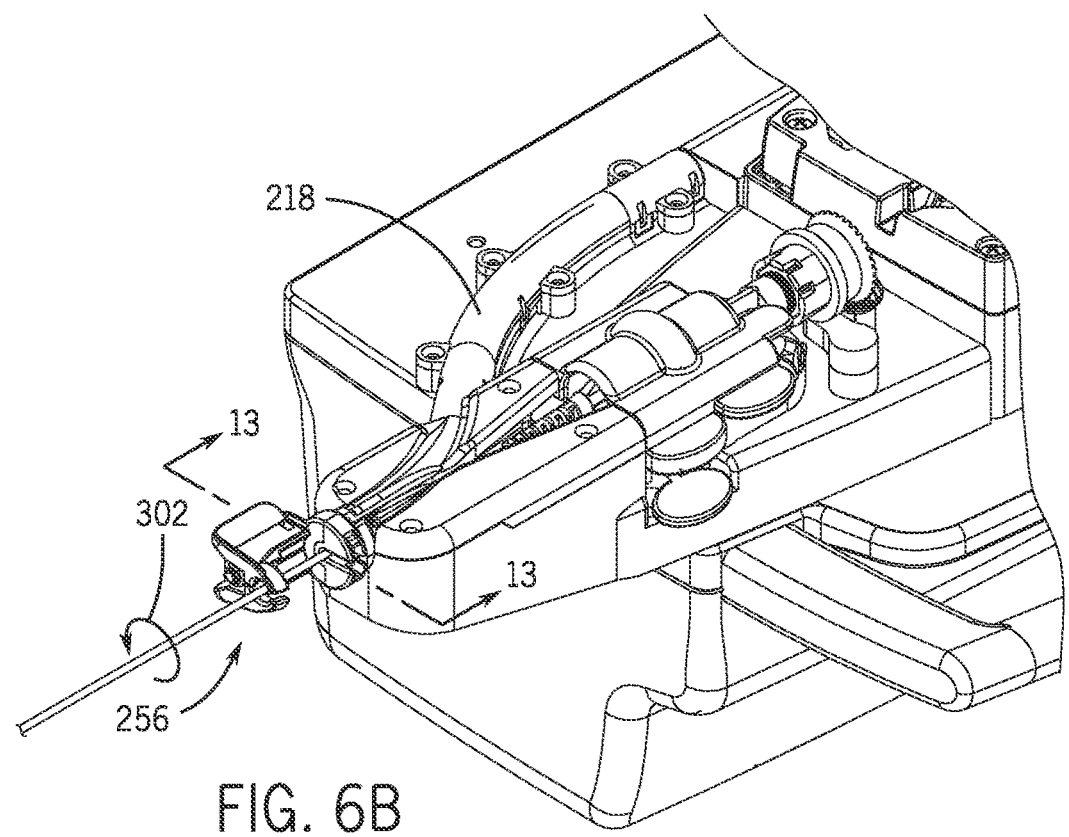
FIG. 6B is an isometric view of the robotic catheter system with the sheath clip in an engaged position.
Figure 13:
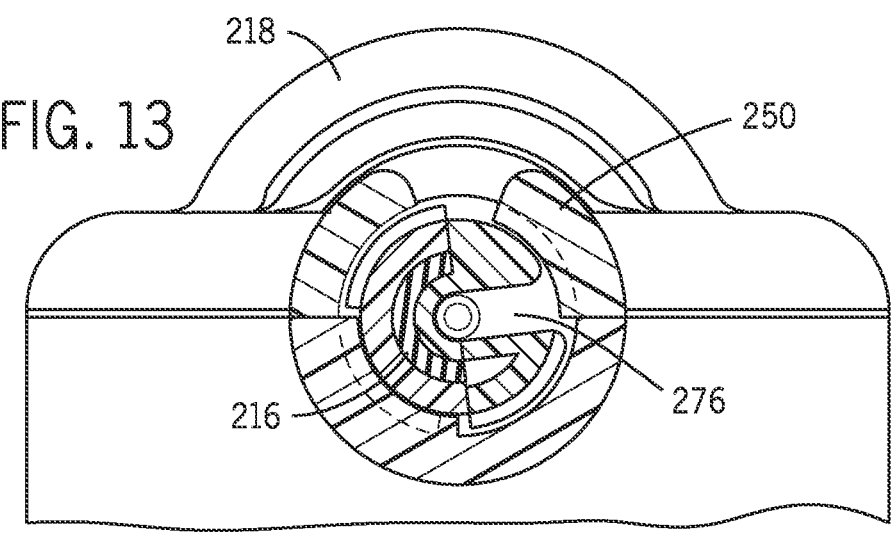
FIG. 13 is a cross-sectional view of the front portion of the robotic catheter system taken generally along lines 13-13 of FIG. 6B with the sheath clip in the operational position.

Referring to FIG. 6B and FIG. 13, in one embodiment sheath clip 256 is rotated about longitudinal axis 248 until opening 276 extends 90 degrees from the vertical orientation shown in FIG. 12. In this manner guide catheter 228 is assisted in remaining within the channel of flexible track 216. As sheath clip 256 is rotated 90 degrees, extension member 298 acts to widen the opening defined by slit 286 immediately adjacent the longitudinal axis 248. In this manner guide catheter 228 can enter and exit flexible track 216 without interference from the edges of the flexible track that defines slit 286. In one embodiment described below a sheath clip 420 does not need to be rotated but simply pulled distally away from cassette 222.

In one embodiment sheath clip 256 is rotated in a first direction 90 degrees illustrated in FIG. 6B, while in another embodiment sheath clip 256 is rotated 90 degrees in a direction opposite to the direction. It is also contemplated that sheath clip 256 may be rotated less than or greater than 90 degrees. In one embodiment described below sheath clip 420 does not need to be rotated.

Referring to FIG. 14 and FIG. 15 in one embodiment once sheath clip 256 has been rotated to the operation position shown in FIG. 13, the sheath clip is pulled by a user away from cassette 222 in a direction along longitudinal axis 248 until the distal end 280 sheath clip 256 is proximate the patient. In one embodiment an introducer is secured to distal end 280 of sheath clip 256. The introducer is a device that is secured to a patient to positively position the introducer to the patient to allow insertion and removal of elongated medical devices such as the guide catheter, guide wire and or working catheter into the patient with minimal tissue damage to the patient. Once the operator has pulled the sheath clip and accompanying flexible track toward the patient such that the introducer is proximate the patient, the flexible track is locked in position by a locking clamp 310.

Figure 18:
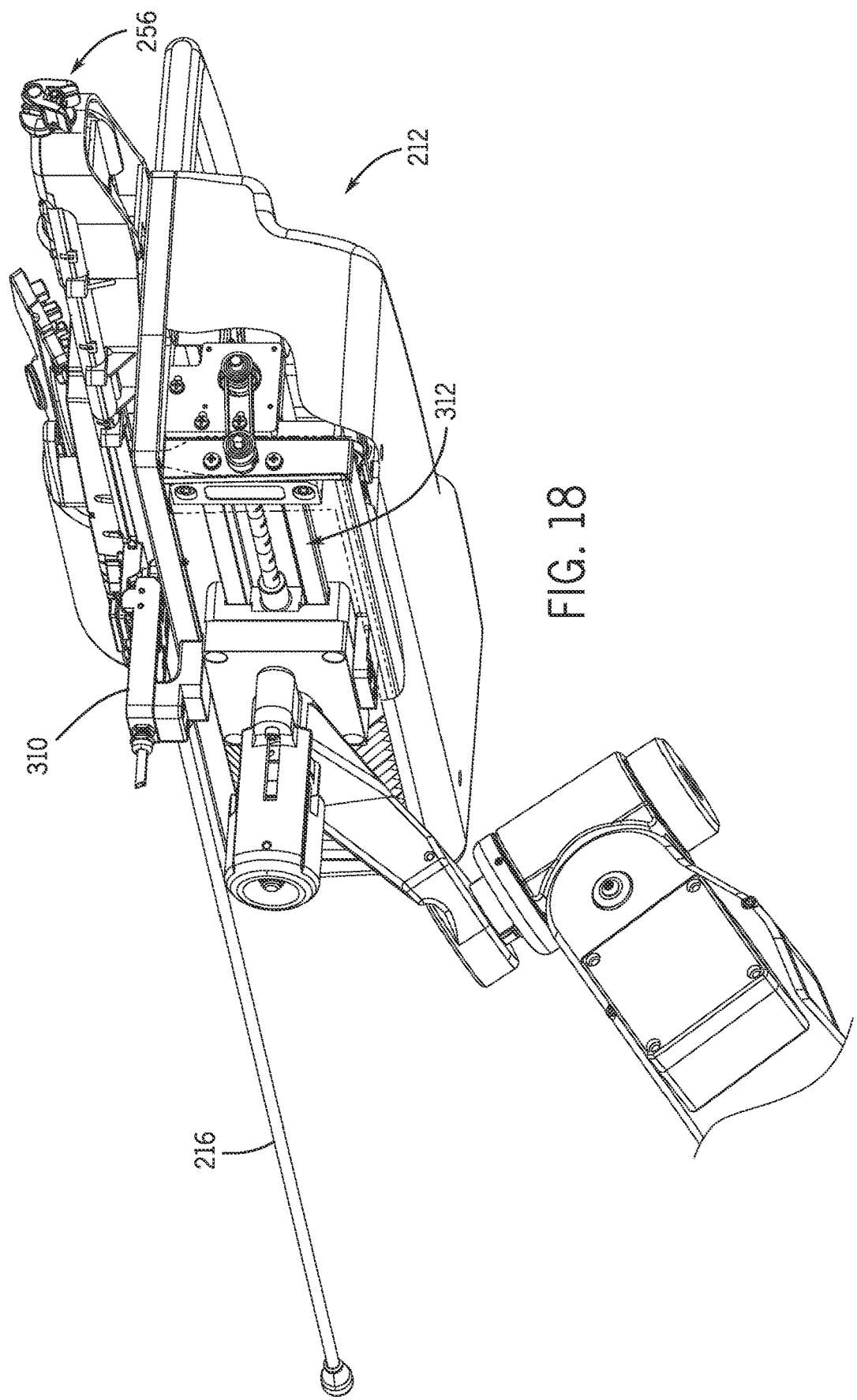
FIG. 18 is a rear isometric view of the robotic catheter system with a linear drive.
Figure 19:
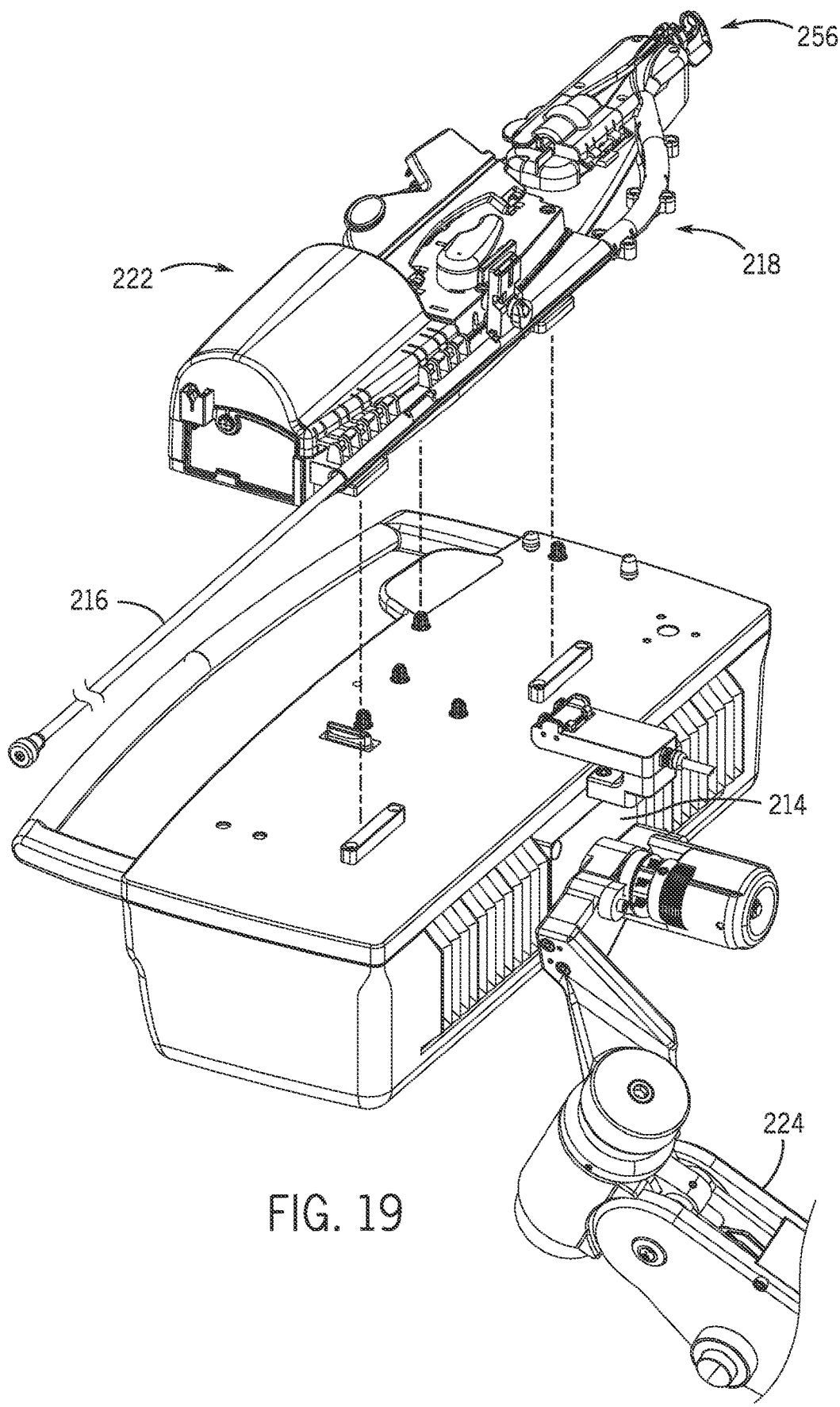
FIG. 19 is an exploded rear isometric view of the robotic catheter system with the cassette in a pre-assembly position relative to the robotic drive base.
Figure 22:
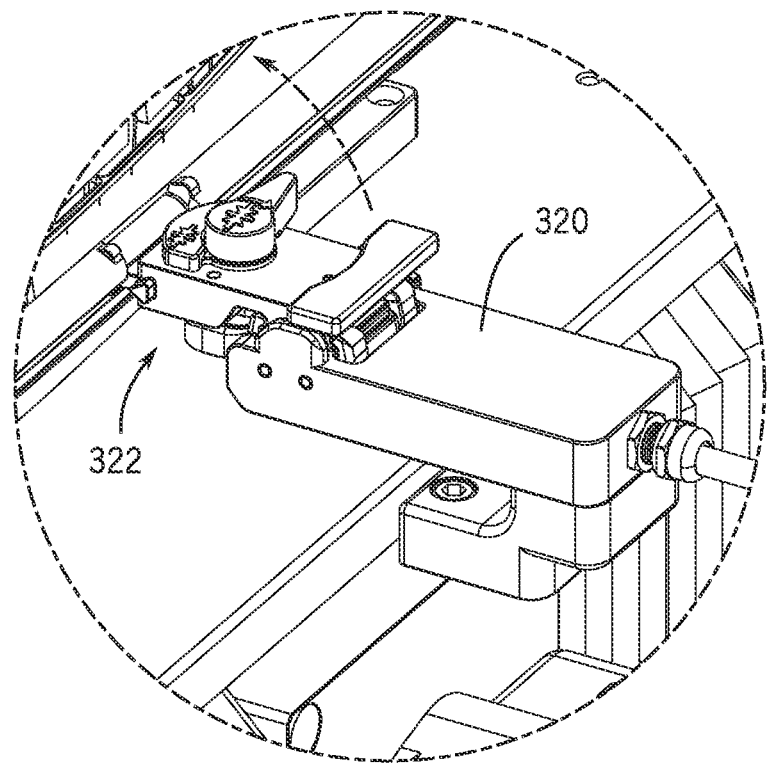
FIG. 22 is a close-up isometric view of the locking track clamp in an engaged position.
Figure 23:
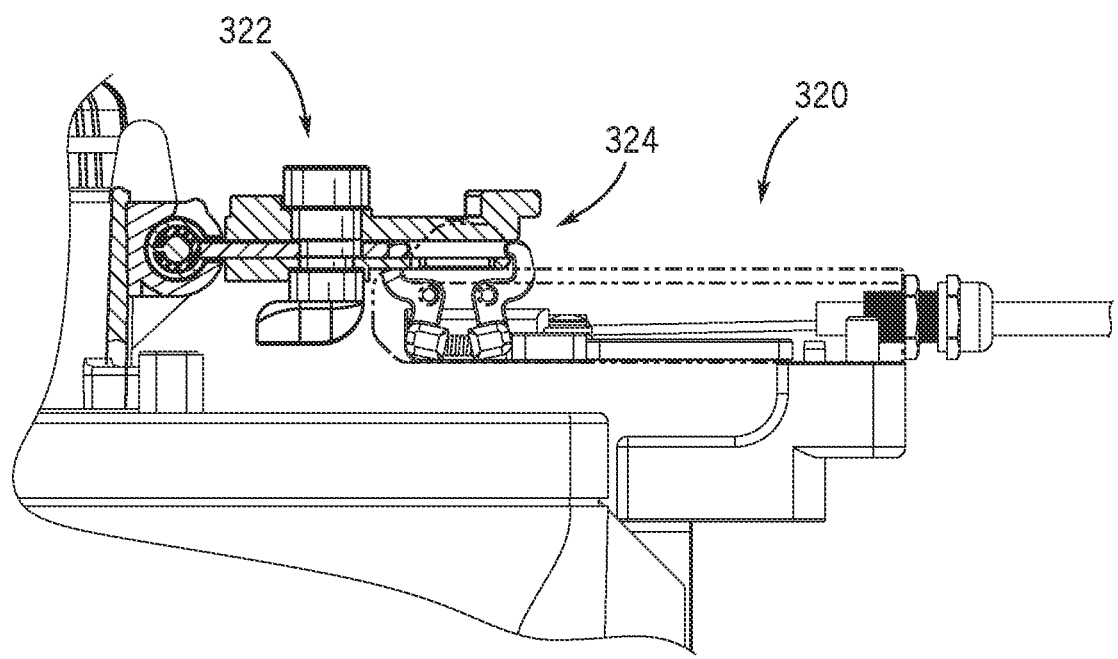
FIG. 23 is a cross-sectional view of the locking track clamp in an engaged position and unlocked.

Locking clamp 310 secures flexible track 216 to base 214 such that a portion of flexible track 216 is in a fixed position relative to the patient bed and the patient to the extent the patient lies still on the patient bed. Referring to FIG. 18, a linear drive mechanism 312 includes a linear slide that is robotically controlled by a user through a remote control station. Catheter drive mechanism drive 312 drives robotic mechanism 212 along longitudinal axis 248. Since rigid guide 218 is fixed relative to robotic mechanism 212, flexible track 216 moves relative to the rigid guide 218 as the robotic mechanism 212 moves along the longitudinal axis 248.

Referring to FIGS. 14, 15, 16 and 17 the operation and movement of flexible track 216 relative to rigid guide 218 will be described. Referring to FIG. 14 flexible track 216 is shown in the installation first position in which guide catheter 228 is positioned within sheath clip 256 and flexible track opening 274 as described above. Referring to FIG. 15, once sheath clip 256 has been released from the cassette 222 as described above the sheath clip 256 and distal end of the flexible track are pulled by a user away from cassette 222 such that the distal end of the sheath clip 256 is proximate the entry point of the patient in which a percutaneous intervention will occur. As described below in further detail locking clamp 310 operatively clamps a portion of flexible track 216 that flexible track 216 fixed relative to base 214.

Referring to FIGS. 14 and 15 the portion of flexible track 216 that is positioned within arcuate portion of rigid guide 218 is pulled out of the distal end of rigid guide 218 in a direction generally along longitudinal axis 248. Similarly, a portion 322 of flexible track 216 that was external to and not located within the arcuate portion of rigid guide 218 is pulled into the arcuate portion of rigid guide 218 and depending on how far the terminal end of the flexible track is pulled toward the patient portion 322 of flexible track 216 will enter the arcuate portion of rigid guide 218 and may extend therefrom. Stated another way flexible track 216 includes three general regions that change with the operation of the guide catheter system. First a proximal region that includes the flexible track portion from the proximal end 253 to the opening 324 of the arcuate portion of rigid guide 218. Flexible track 216 includes a second portion located between the proximal end 324 of the arcuate portion of rigid guide 218 and the distal end 325 of the arcuate portion of rigid guide proximate collar 250. Flexible track includes a third region that extends from collar 250 of rigid guide 218 in a direction defined by a vector generally along longitudinal axis 248, where the vector has a beginning at Y-connector and extends in a direction toward collar 250.

The first region and second region of flexible track 216 as described above is offset from and not in line with longitudinal axis 248. The third portion of flexible track 216 is generally coaxial with longitudinal axis 248 as flexible track 216 exits collar 250 of rigid guide 218.

During one type of intervention procedure, guide catheter 228 is inserted into a patient's femoral artery through an introducer and positioned proximate the coronary ostium of a patient's heart. An operator may wish to relocate the distal end of the guide catheter robotically. Referring to FIG. 16 and FIG. 17 the control of the distal end of guide catheter 228 will be described. Referring to FIG. 16 guide catheter 228 has a distal portion which extends beyond the distal end of sheath clip 256 in order to extend beyond the terminal end of guide catheter 228 in a direction away from the terminal end of sheath clip. As noted above the distal end of guide catheter 228 may be placed proximate the ostium of a patient. The robotic control of the distal end of guide catheter 228 is accomplished by movement of robotic drive mechanism 212 relative to base 214 by linear drive 312. Guide catheter is located within the channel of the flexible track from cassette 222 until the sheath clip 256. Since flexible track 216 is secured relative to base 214 the second portion of flexible track 216 as described above will move from within the arcuate portion of rigid guide 218 to a position offset from longitudinal axis 248. Similarly, a third portion of flexible track 216 that extended distally beyond collar 250 will be retracted and moved into the arcuate portion of rigid guide 218 and in doing so is moved away from and offset from longitudinal axis 248.

If during a PCI procedure guide catheter begins to slip out of the ostium it is possible to extend the distal end of guide catheter 228 back into the patient's ostium by robotically moving the robotic drive 212 toward the patient. In doing so the distal end of guide catheter 228 is moved toward the patient reinserting or seating the distal end of the guide catheter into the patient's ostium as one example. As the robotic drive mechanism 212 is moved along longitudinal axis 248 flexible track 216 is moved relative to rigid guide 218. In actual operation a portion of flexible track 216 is fixed in space relative to base 214 at locking clamp 310. However, the portion of flexible track 216 that is located within the arcuate section of rigid guide 216 is moved toward and away from longitudinal axis 248 depending on the direction that the robotic drive mechanism 212 is moving. Guide catheter 228 moves into or out of the section of the flexible track 216 that is moving in and out of the arcuate portion of rigid guide 218. In this manner the portion of the guide catheter 228 between cassette 222 and the sheath clip is always located within the channel of flexible track 216. In this manner guide catheter 228 may be manipulated within flexible track 216 without buckling or causing other non-desirable movement during a percutaneous intervention procedure.

Referring to FIG. 16 and FIG. 17 the movement of flexible track 216 with respect to rigid guide 218 will be described as it relates to single section A on flexible track 216. In one example section A on flexible track 216 is located distal collar 250 of rigid guide 218. When an operator determines to insert guide catheter 228 further into or toward a patient in a direction away from collar 250 an input device is manipulated by the user at a remote control station that drives robotic drive 212 distally along longitudinal axis 248 by activating linear drive 312. The proximal end of guide catheter 228 is longitudinally fixed in cassette 222 by clamp 310 so that as the robotic drive 312 including cassette 222 is moved relative to base 214 by linear drive 312, in a direction toward the patient guide catheter 228 moves distally along longitudinal axis 248. As a result, the distal end of guide catheter 228 moves toward and/or into the patient.

As the robotic drive mechanism is moved along longitudinal axis 248 section A of flexible track 216 moves into rigid guide 218 through collar 250 and is moved along the arcuate portion of rigid guide 218 until section A of the flexible track 216 is adjacent the proximate opening of rigid guide 218. In this manner distal end of flexible track remains in a constant position but section A of flexible track 216 is moved out of or offset to the longitudinal axis 248. As section A moves from a point proximate the collar 250 into the arcuate channel defined by the rigid guide 218 the guide catheter 228 enters the channel or hollow lumen of the flexible track 216 through the slit adjacent in the engagement zone proximal to collar 250. In this manner flexible track 216 provides continual support and guidance for the guide catheter 228 between the collar 250 and patient as the distal end of guide catheter 228 is moved toward and away from the patient.

Similarly, if the operator desires to retract the distal end of the guide catheter 228 from within the patient, the user provides a command to the linear drive through the remote control station to move robotic drive mechanism 212 in a direction away from the patient. In this way section A of the flexible track 216 would enter the proximal end of the arcuate portion of the rigid guide and be guided within the channel of the rigid guide 218 until section A exits the distal end of the rigid guide 218. The guide catheter 228 would enter the slit at section A or stated another way a portion of the guide catheter 228 would enter the flexible track 216 via the portion of the slit that is located within the concentric circle taken at section A of the flexible track. Note that although sections of flexible track are positioned in different regions of the rigid guide as the robotic mechanism in moved toward and away from the patient the proximal end and the distal end of the flexible track remain in a fixed location as the robotic mechanism is moved along the longitudinal axis.

Referring to FIGS. 19-26 locking clamp 310 includes a base portion 320 operatively connected to base 214 and a clamp portion 322 that is coupled to base portion 320 via an engagement mechanism 324. Engagement mechanism 324 includes a pair of clasps 370, 371 on base portion 320 that engage a portion 357 via two indentations or grooves 360 and 362 on clamp portion 322. Clamp portion 322 includes a body 326 having a rigid guide connector 328 that is pivotally received in an opening in the rigid guide. Connector 328 includes a cylindrical member 356 that is received within the opening in rigid guide 218. Referring to FIG. 21 Clamp portion 322 is in a raised position that can be used to ship the cassette separately from robotic drive base 220 without clamp portion 322 extending outwardly or rearwardly from cassette 222. Clamp portion 322 pivots about the longitudinal axis of rigid guide 218 proximate the opening in rigid guide 218 to an outwardly orientation to be coupled to base portion 320.

Figure 26A:
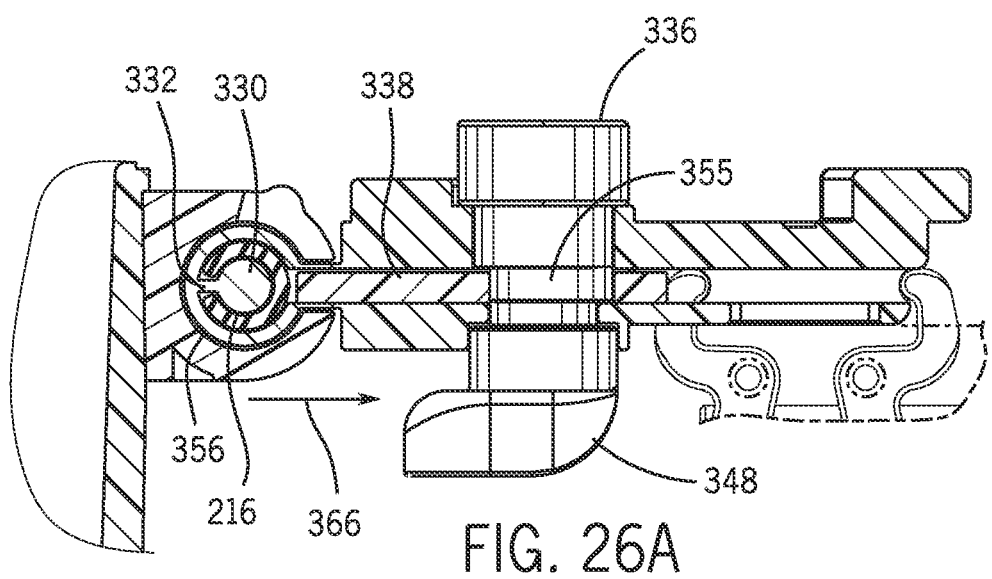
FIG. 26A is a cross-sectional view of the locking track clamp in an unlocked position.

Referring to FIG. 24, cylindrical member 356 defines a channel extending therethrough through which flexible track 216 extends. Extending inwardly into the channel from the cylindrical member 356 is a flat support 332. An inner cylindrical guide member 330 extends from flat support 332 such that cylindrical guide member is coaxial with the cylindrical member 356. Flexible track 216 is threaded through a proximal opening in rigid guide 218 and is passed over inner cylindrical guide member 330 such that the slit in flexible track 216 passes over flat support 332. In this manner flexible track 216 is positioned between inner cylindrical guide member 330 and cylindrical member 356. Referring to FIG. 26A cylindrical member 356 includes a longitudinal opening through which a cam member 338 extends from body 326 toward the region defined between the inner cylindrical guide member 330 and the cylindrical member 356. As described below cam member 338 acts to lock flexible track 216 against inner cylindrical guide member 330.

Cam lock portion 322 includes a handle member 334 having a handle portion 354 and bearing surface 358 and a cam portion 355. Handle member 334 includes a keyed post 352 that is connected to a bottom key receptacle 344 through keyed opening 350. A fastener secures handle 334 to bottom key receptacle 344. Body 326 includes an opening 336 through which bearing 358 and cam 355 extend. Cam plate 338 includes an aperture 342 having an inner surface. Cam plate 338 includes a locking surface 340. In operation cam plate 342 is positioned within a slot in body 326 such that opening 342 is aligned with opening 336.

Figure 25A:
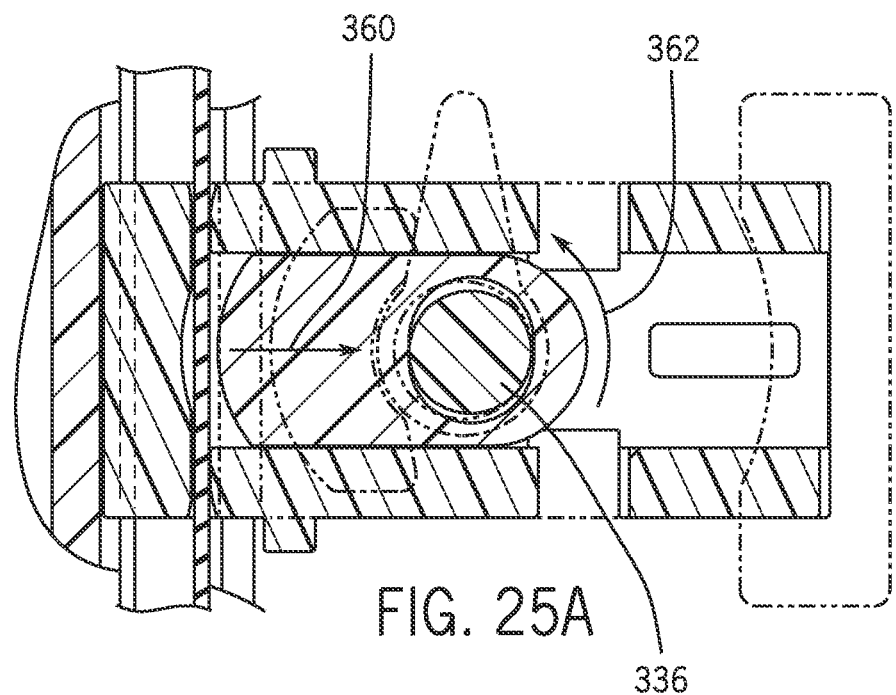
FIG. 25A is a cross-sectional view of the locking track clamp in an unlocked position.
Figure 25B:
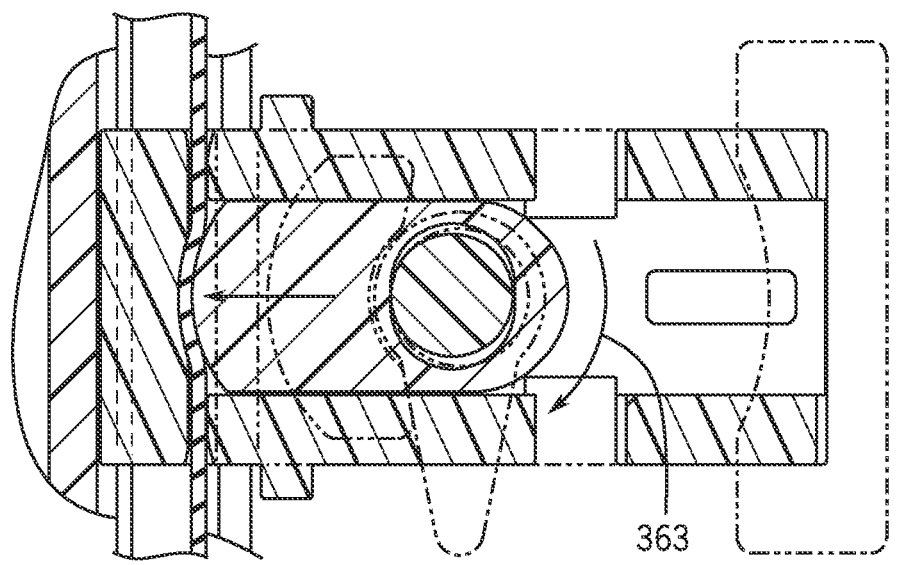
FIG. 25B is a cross-sectional view of the locking track clamp in a locked position.
Figure 26B:
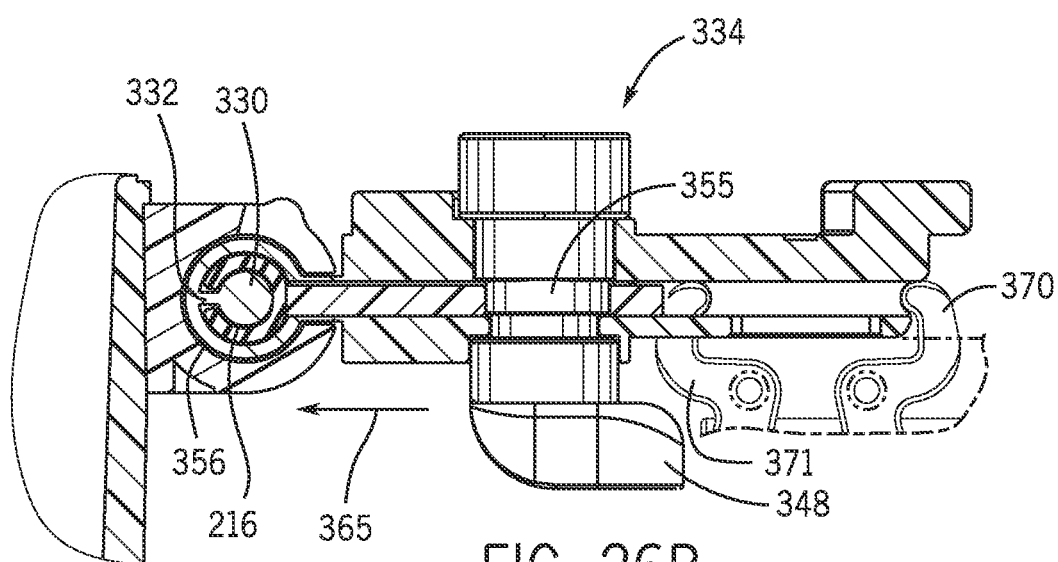
FIG. 26B is a cross-sectional view of the locking track clamp in the locked position.

Referring to FIGS. 25A, 26A in the unlocked position lock surface 340 does not abut flexible track 216. Referring to FIGS. 25B and 26B bearing member 358 cooperates with the wall of opening 336 to centrally locate handle 334 within opening 336. Cam member 355 is positioned within opening 342 of cam plate 338 such that when handle 334 is rotated locking surface 340 is moved toward and away from rigid guide 218 to operatively y lock and unlock flexible track 216 relative to lock 310 and thereby to base 214.

Figure 29:
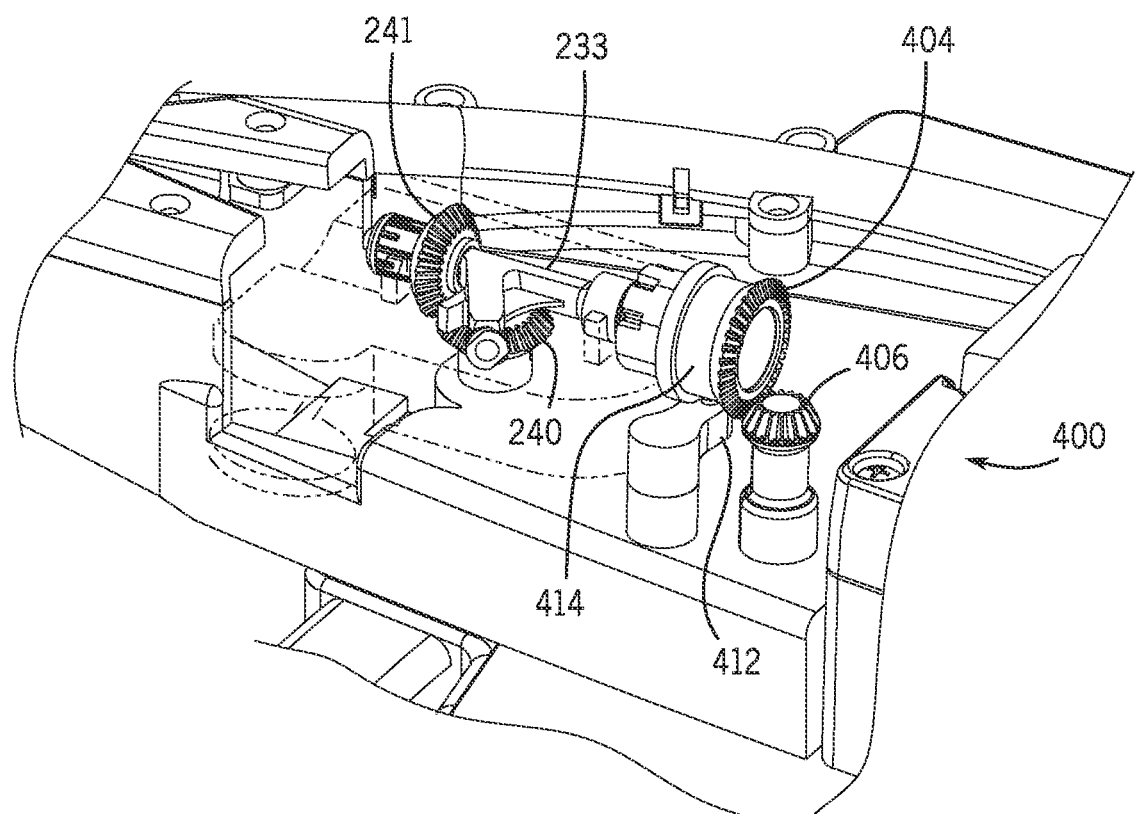
FIG. 29 is a view of a hemostasis valve control mechanism.
Figure 30:
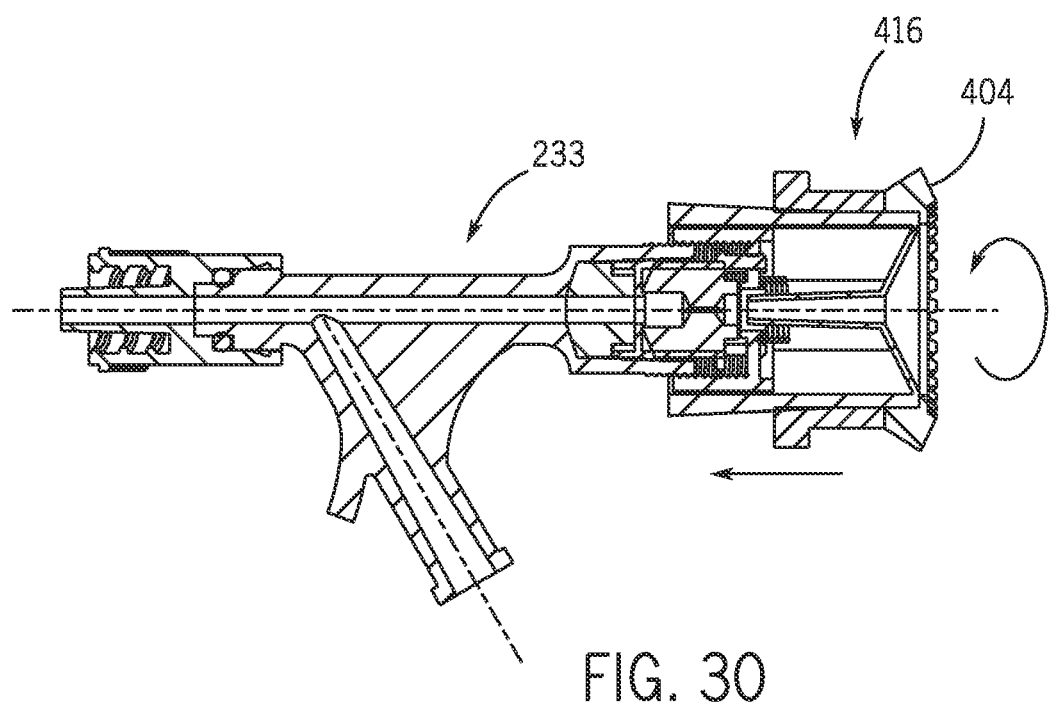
FIG. 30 is a cross-sectional view of the hemostasis valve illustrating the opening and closing the back portion of the hemostasis valve.

Referring to FIGS. 29 and 30 Y-connector 233 is a hemostasis valve 402 that includes a valve body with a first leg having a proximal port, a distal port and a lumen extending between the proximal port and the distal port. At least one valve is located in the lumen adjacent the proximal port to permit an interventional device to be passed therethrough. The valve body includes a second leg extending at an angle relative to the first leg and in fluid communication with the first leg. A rotating male luer lock connector is rotatably connected to the valve body proximate the distal port to secure proximal end of guide catheter 228 thereto.

In one embodiment hemostasis valve 402 includes a bleedback valve used to reduce the blood that may be lost during an interventional procedure. The bleedback valve acts to allow an elongated device such as a guide wire to extend therethrough but minimizes blood loss through the valve. In one embodiment hemostasis valve 402 includes a Tuohy-Borst adapter that allows for the adjustment of the size of the opening in proximal end. Rotation of an engagement member about the valve's longitudinal axis acts to increase or decrease the diameter of the opening.

In one embodiment the bleedback valve is opened from a closed position to a fully opened position with a single motion or translation of an engagement member. In one example an engagement member is push or pulled along the longitudinal axis of the elongated medical device to fully open or fully close the valve. Some hemostasis valve devices include both type of controls, a rotational engagement member that opens and closes the tuohy borst valve by rotation of the engagement member about the longitudinal axis of the engagement member and a push pull control in which the engagement member is moved along the longitudinal axis to open and close the bleedback valve. Other type of control mechanisms are also known such as using a lever or ratchet to open and close the valve.

Referring to FIG. 29 and FIG. 30 hemostasis valve 402 includes an engagement member 416 that provides operation of the Tuohy-Borst valve by rotation of engagement member 416 and a push pull adjustment of the bleedback valve between a fully open and closed position by moving the engagement member 416 along the longitudinal axis of the hemostasis valve.

Control of the Tuohy-Borst and bleed back valves is accomplished robotically from a remote control station 14 by a first drive member 406 operatively connected to a first driven member 404 to rotate engagement member about the longitudinal axis. In one embodiment first drive member is a drive gear and the driven member 404 is a beveled gear secured to engagement member 416 and operatively connected to a drive gear. A second drive member 412 is operatively connected to the engagement member to translate the engagement member 416 along the longitudinal axis of the hemostasis valve. In one embodiment, second drive member is a lever that is robotically controlled via a motor that is controlled by the remote control station 14. Lever 412 operatively engages a collar slot 414 in the outer periphery of engagement member 16 such that movement of the lever 412 results in the translation of the engagement member 416 which as discussed above opens the bleedback valve between the closed and open positions.

In one embodiment a user may operate the first drive member 412 and the second drive member 412 to open and close the bleedback and Tuohy-Borst valves by providing instructions through a user input to rotate and/or translate the engagement member 416 about and/or along the longitudinal axis. In one embodiment, first drive member 412 and the second drive member 412 are automatically operated by a remote robotic control station 14 in response to a sensor that senses the blood flow and/or fictional forces required to move an elongated medical device either through the hemostasis valve and or a patients' vasculature. When the system detects that the force required to robotically rotate and or translate the elongated medical device the system reaches some predetermined value the processor would provide instructions to incrementally open and or close the opening in one or both of the valves. Monitoring of a patient's blood pressure and or whether blood is being lost through the valve would be used as factors in an algorithm to determine the appropriate adjustment to the opening in the valves.

Referring to FIG. 27, robotic catheter system 210 operates proximate a patient bedside system 12 adjacent a patient bed 22. A remote work station 14 includes a controller 16, a user interface 18 and a display 20. An imaging system 24 may be any medical imaging system that may be used in conjunction with a catheter based medical procedure (e.g., non-digital x-ray, digital x-ray, CT, MRI, ultrasound, etc.). In one embodiment, imaging system 24 is a digital x-ray imaging device that is in communication with workstation 14. Imaging system 24 is configured to take x-ray images of the appropriate area of patient during a particular procedure. For example, imaging system 24 may be configured to take one or more x-ray images of the heart to diagnose a heart condition. Imaging system 24 may also be configured to take one or more x-ray images during a catheter based medical procedure (e.g., real-time images) to assist the user of workstation 14 to properly position a guide wire, guide catheter, and a working catheter such as a stent during a procedure. The image or images may be displayed on display 20 to allow the user to accurately position a distal tip of a guide wire or working catheter into proper position in a patient's vasculature.

Referring to FIG. 28 flexible track 216 extends along the longitudinal axis 248 toward the patient. However, during a procedure the patient may move resulting in the sheath clip pulling away or toward the patient. In one embodiment flexible track 216 assumes an arc shape between the distal end of cassette 222 and the patient. Guide catheter 228 positioned within the cavity defined by flexible track 216 assumes the same arc shape as flexible track 216. If a patient moves during a procedure the away from cassette 222 the arc 390 will flatten. Similarly, if the patient moves during the procedure toward the cassette 222 the arc 390 will be more pronounced. In both circumstances flexible track 216 prevents guide catheter 228 from buckling during a PCI procedure.

Referring to FIG. 30 in one embodiment a sheath clip 420 is positively received within a distal end of cassette 222. The distal end of flexible track 216 is secured to a sheath clip 410 adjacent radially extending handle portion 428, sheath clip 420 includes a groove 430 having an opening 432. The distal end of flexible track 216 is located within the bottom of groove 430. In the install position shown in FIG. 31 the longitudinal axis of sheath clip 420 is co-axial with longitudinal axis 248 of robotic mechanism 212. Top position the sheath clip 420 and flexible track 216 in an operation position a user pulls handle portion 428 and extends sheath clip 420 and attached flexible track 216 in a direction away from the robotic mechanism 212 and toward a patient. In one embodiment there is no need to rotate guide sheath 420 relative to cassette 222. A user simply pulls sheath clip 420 distally in a direction away from robotic mechanism 212.

Referring to FIG. 32 and FIG. 33, sheath clip 420 includes an introducer sheath connector 424 that releasably engages an introducer sheath 422. Introducer sheath connector includes at least a portion that rotatably coupled to sheath clip 420 proximate handle portion 428. Introducer sheath connector 424 includes an arm 436 that releasably engages an outer surface of introducer 422 to operatively couple the introducer sheath to sheath clip 420. Arm 436 in the engaged position illustrated in FIG. 33 prevents introducer sheath 422 from moving from sheath clip 420 along the longitudinal axis toward or away from the patient. A tube extending from introducer sheath 422 is captured between sheath clip 420 and arm 436.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

What is claimed is:

1. A system for controlling a hemostasis valve comprising:
   a hemostasis valve comprising:
      a body portion having a proximal end, a distal end and a lumen extending between the proximal end and the distal end;
      at least one valve positioned in the proximal end of the body portion; and
      an engagement member operatively coupled to the at least one valve;
   the body portion of the hemostasis valve being pivoted from a raised position to an-in use position,
   a first drive member removably coupled to the engagement member as the body portion of the hemostasis valve is pivoted to the in-use position and uncoupled from the engagement member as the hemostasis valve is pivoted to the raised position; and
   a controller coupled to the first drive member, the controller configured to control the first drive member to impart movement to the engagement member to open and close the at least one valve.

2. The system according to claim 1, wherein the controller is configured to incrementally adjust an amount the at least one valve is opened or closed.

3. The system according to claim 1, wherein the first drive member imparts rotational movement to the engagement member; the engagement member rotates in a plane perpendicular to the longitudinal axis of the hemostasis valve.

4. The system according to claim 1, wherein the first drive member imparts linear movement to the engagement member.

5. The system according to claim 1, wherein the at least one valve is a Tuohy-Borst valve.

6. The system according to claim 1, wherein the at least one valve is a bleedback valve.

7. The system according to claim 1, wherein the at least one valve includes a bleedback valve and a Tuohy-Borst valve.

8. The system according to claim 1 further including a base and a support member supporting and pivoting the body portion of the hemostasis valve relative to the base from the raised position to the in-use position, wherein the body portion has a longitudinal axis that is in a first orientation relative to the base in the in-use position and a second orientation that non-colinear with the first orientation in the raised position.

9. A system for controlling a hemostasis valve comprising:
   a base, and
   a hemostasis valve comprising:
      a body portion having a proximal end, a distal end and a lumen extending between the proximal end and the distal end;
      at least one valve positioned in the proximal end of the body portion; and
      an engagement member operatively coupled to the at least one valve;
   the body portion being pivotable between a raised position to uncouple the engagement member to a drive member and an-in use position to couple the engagement member to the drive member, wherein the body portion has a longitudinal axis that is in a first orientation relative to the base in the in-use position and a second orientation that non-colinear with the first orientation in the raised position;
   a sensor configured to detect at least one of blood flow or a frictional force; and
   a controller coupled to the sensor and the engagement member, the controller configured to automatically control the drive member to operate the at least one valve based on the blood flow or frictional force detected by the sensor.

10. The system according to claim 9, wherein the controller is configured to incrementally adjust an amount the at least one valve is opened or closed.

11. The system according to claim 9, wherein the at least one valve is a Tuohy-Borst valve.

12. The system according to claim 11, wherein the controller rotates the engagement member about a longitudinal axis of the hemostasis valve to increase or decrease a size of an opening of the at least one valve.

13. The system according to claim 9, wherein the at least one valve is a bleedback valve.

14. The system according to claim 13, wherein the controller translates the engagement member along a longitudinal axis of the hemostasis valve to open and close the at least one valve.

15. The system according to claim 9, wherein the at least one valve includes a bleedback valve and a Tuohy-Borst valve.

16. The system according to claim 9 further including a support member moveably supporting the hemostasis valve from the raised position to the in-use position.

17. A system for controlling a hemostasis valve comprising:
 a hemostasis valve comprising:
  a body portion having a proximal end, a distal end and a lumen extending between the proximal end and the distal end;
  at least one valve positioned in the proximal end of the body portion; and
  an engagement member operatively coupled to the at least one valve;
 a sensor configured to detect a frictional force required to move an elongated medical device; and
 a controller coupled to the sensor and the engagement member, the controller configured to control the engagement member to operate the at least one valve based on the detected frictional force, wherein the sensor detects the frictional force required to robotically rotate the elongated device.

18. The system of claim 15, wherein the controller automatically provides instructions to incrementally open or close the valve when the frictional force required to move the elongated medical device reaches a predetermined value.

19. The system of claim 18, wherein the instructions to incrementally open or close the valve are based on both the frictional force required to move the elongated medical device through the valve and a patient's blood pressure.

* * * * *